(12) United States Patent
Webster et al.

(10) Patent No.: US 6,600,996 B2
(45) Date of Patent: *Jul. 29, 2003

(54) COMPUTER-AIDED TECHNIQUES FOR ANALYZING BIOLOGICAL SEQUENCES

(75) Inventors: Teresa A. Webster, Loma Mar, CA (US); MacDonald S. Morris, Felton, CA (US); Michael P. Mittmann, Palo Alto, CA (US); David J. Lockhart, Mountain View, CA (US); Ming-Hsiu Ho, San Jose, CA (US); Derek Bernhart, Sunnyvale, CA (US); Luis C. Jevons, Sunnyvale, CA (US)

(73) Assignee: Affymetrix, Inc., Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/828,952

(22) Filed: Mar. 28, 1997

(65) Prior Publication Data

US 2002/0183933 A1 Dec. 5, 2002

Related U.S. Application Data

(63) Continuation-in-part of application No. PCT/US96/14839, filed on Sep. 13, 1997, and a continuation-in-part of application No. 08/531,137, filed on Oct. 16, 1995, now Pat. No. 5,974,164, which is a continuation-in-part of application No. 08/529,115, filed on Sep. 15, 1995, now Pat. No. 6,040,138, which is a continuation-in-part of application No. 08/327,525, filed on Oct. 21, 1994, now Pat. No. 5,795,716.

(60) Provisional application No. 60/033,053, filed on Dec. 12, 1996.

(51) Int. Cl.$^7$ .................. G01N 33/48; G01N 33/50
(52) U.S. Cl. ............... 702/20; 702/19; 435/6; 435/91.1; 435/91.2; 435/7.1; 435/7.2; 435/23.1; 382/178; 382/179
(58) Field of Search ............... 435/6, 91.1, 91.2, 435/7.1, 7.2, 23.1; 382/178, 179; 702/19, 20

(56) References Cited

U.S. PATENT DOCUMENTS

| | | | |
|---|---|---|---|
| 4,741,043 A | 4/1988 | Bacus | 382/6 |
| 4,965,725 A | 10/1990 | Rutenberg | 364/413.1 |
| 4,981,783 A * | 1/1991 | Augenlicht | 435/6 |
| 5,002,867 A | 3/1991 | Macevicz | 435/6 |
| 5,143,854 A | 9/1992 | Pirrung et al. | 436/518 |
| 5,202,231 A | 4/1993 | Drmanac et al. | 435/6 |
| 5,235,626 A | 8/1993 | Flamholz et al. | 378/34 |
| 5,273,632 A | 12/1993 | Stockham | 204/180 |
| 5,288,514 A | 2/1994 | Ellman | 427/2 |
| 5,384,261 A | 1/1995 | Winkler et al. | 436/518 |
| 5,424,186 A | 6/1995 | Fodor et al. | 435/6 |
| 5,445,934 A | 8/1995 | Fodor et al. | 435/6 |
| 5,460,908 A | 10/1995 | Reinberg | 430/5 |
| 5,470,710 A | 11/1995 | Weiss et al. | 435/6 |
| 5,492,806 A | 2/1996 | Drmanac et al. | 435/5 |
| 5,502,773 A | 3/1996 | Tibbetts et al. | 382/129 |
| 5,525,464 A | 6/1996 | Drmanac et al. | 435/6 |
| 5,527,681 A | 6/1996 | Holmes | 435/6 |
| 5,733,729 A * | 3/1998 | Lipshutz et al. | 435/6 |
| 5,795,716 A * | 8/1998 | Chee et al. | 435/6 |
| 5,972,619 A * | 10/1999 | Drmanac et al. | 435/6 |
| 5,974,164 A * | 10/1999 | Chee | 382/129 |
| 5,994,076 A * | 11/1999 | Chenchik et al. | 435/6 |
| 6,040,138 A * | 3/2000 | Lockhart et al. | 435/6 |
| 6,066,454 A * | 5/2000 | Lipshutz et al. | 435/6 |
| 6,232,068 B1 * | 5/2001 | Linsley et al. | 435/6 |
| 6,268,147 B1 * | 7/2001 | Beattie et al. | 435/6 |
| 6,344,316 B1 * | 2/2002 | Lockhart et al. | 435/6 |

FOREIGN PATENT DOCUMENTS

| | | |
|---|---|---|
| EP | 0 721 016 | 7/1996 |
| WO | WO 89/10977 | 11/1989 |
| WO | WO 92/10092 | 6/1992 |
| WO | WO 92/10588 | 6/1992 |
| WO | WO 95/11995 | 5/1995 |
| WO | 95/11995 | 5/1995 |
| WO | 95/20681 | 8/1995 |

OTHER PUBLICATIONS

D. W. Smith "Biocomputing: Information & Genome Projects". Chap. 2&9; pp. 13–49, 249–167 Acad. Press: NY, 1996.*

Kerkof et al., "A Procedure for Making Simultaneous Determinations of the Relative Levels of Gene Transcripts in Tissues or Cells", Analytical Biochemistry vol. 188 pages 349–355, 1990.*

Southern et al., "Analyzing and Comparing Nucleic Acid Sequences by Hybridzation to Arrays of Oligonucleotides: Evaluation Using Experimental Models", Genomics vol. 13 pp. 1008–1017 1992.*

Chee M. et al., "Accessing Genetic Information with High-Density DNA Arrays" Science, American Association for the Advancement of Science, US, vol. 274, Oct. 25, 1996, pp. 610–614.

(List continued on next page.)

*Primary Examiner*—Mary K. Zeman
(74) *Attorney, Agent, or Firm*—Ritter, Lang & Kaplan LLP

(57) ABSTRACT

Computer-aided techniques for analyzing biological sequences like nucleic acids are provided. The computer system may analyze hybridization intensities indicating hybridization affinity between nucleic acid probes and a sample nucleic acid sequence in order to call bases in the sample sequence. Multiple base calls may be combined to form a single base call. Additionally, the computer system may analyze hybridization intensities in order to monitor gene expression or the change in gene expression as compared to a baseline.

19 Claims, 28 Drawing Sheets

OTHER PUBLICATIONS

Lockhart D.J. et al, "Expression Monitoring by Hybridization to High–Density Oligonucleotide Arrays" Nature Publishing Co., New York, US., vol. 14, No. 13, Dec. 1, 1996, pp. 1675–1680.

Brown Randy et al., "An Inexpensive MSI/LSI Mask Making System," *IEEE Symposium Proceedings 1981*, University Government Industry Microelectronics (UGIM), Sponsored by IEEE, Starkville, Mississippi, pp. III–31 to III–38.

Fodor, Stephen P. A. et al., "Light–Directed, Spatially Addressable Parallel Chemical Synthesis," *Science,* vol. 251, Feb. 15, 1991, pp. 767–773.

Southern, E. M., "Analyzing and Comparing Nucleic Acid Sequences by Hybridization to Arrays of Oligonucleotides: Evaluation Using Experimental Models," *Genomics*, 13, 1992, pp. 1008–1017.

Southern, E. M., "DNA Chips: Analysing Sequence by Hybridization to Oligonucleotides on a Large Scale," *TIG*, Mar. 1996, vol. 12, No. 3, pp. 110–115.

Dear et al., A Sequence Assembly and Editing Program For Efficient Management of Large Projects, Nucleic Acids Research, vol. 19, No. 14, 1991 Oxford Univ. Press, pp. 3907–3911.

* cited by examiner

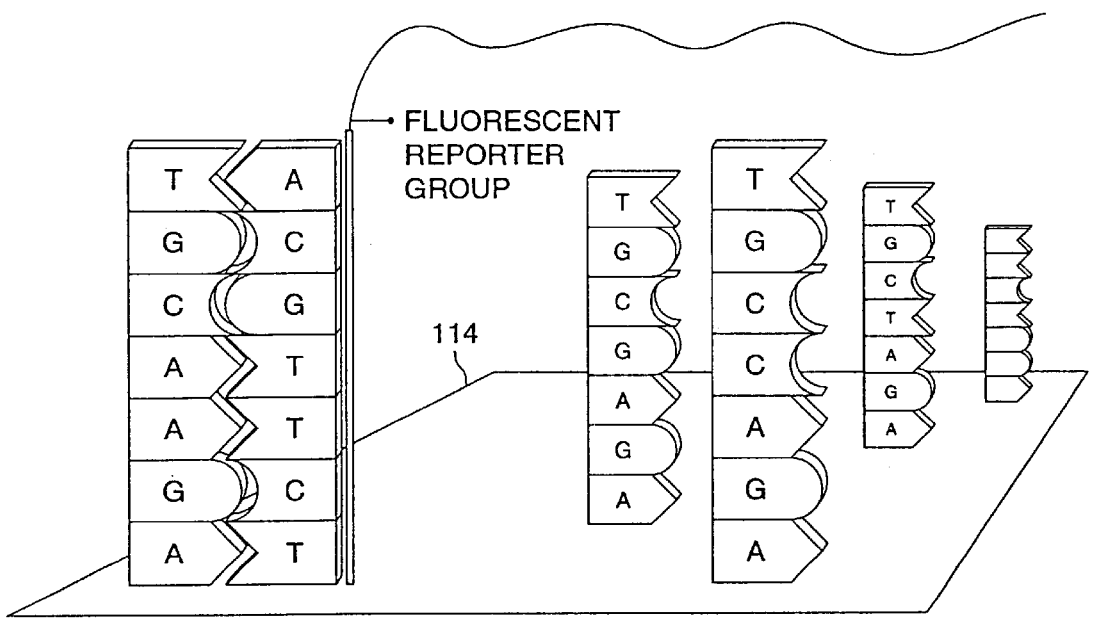
FIG. 6
REFERENCE     A C T₁ G₂ T₃ T₄ A₅ G C T A A T T G G - 5'
SEQUENCE
WT-LANE       T G |A| C    G A |C| A    A C |A| A    C A |A| T    A A |T| G
A-LANE        T G |A| C    G A |A| A    A C |A| A    C A |A| T    A A |A| G
C-LANE        T G |C| C    G A |C| A    A C |C| A    C A |C| T    A A |C| G
G-LANE        T G |G| C    G A |G| A    A C |G| A    C A |G| T    A A |G| G
T-LANE        T G |T| C    G A |T| A    A C |T| A    C A |T| T    A A |T| G
                  I₁          I₂          I₃          I₄          I₅
FIG. 7
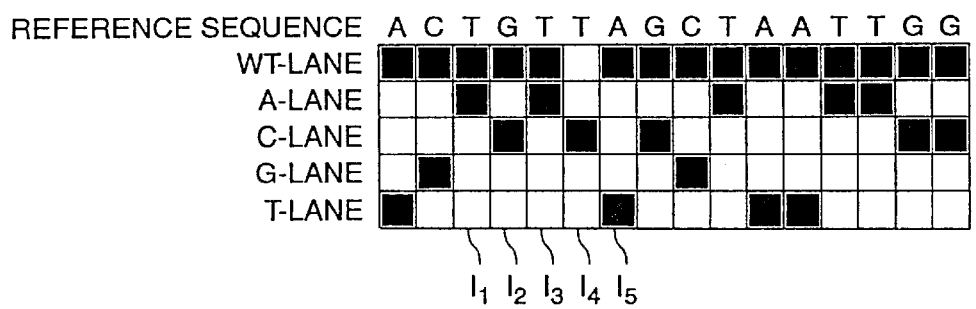
FIG. 8

```
                          SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 1:

ACTGTTAGCT AATTGG                                                       16

(2) INFORMATION FOR SEQ ID NO: 2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 2:

GGAAGCTCTA TTAGATACAG GAGC                                              24

(2) INFORMATION FOR SEQ ID NO: 3:

(i) SEQUENCE CHARACTERISTICS:
        (A) LENGTH: 15 base pairs
        (B) TYPE: nucleic acid
```

```
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 3:

ACGGATGAGA TACGA                                                        15

(2) INFORMATION FOR SEQ ID NO: 4:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 4:

ACTGATGAGA TACGA                                                        15

(2) INFORMATION FOR SEQ ID NO: 5:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 5:

ACGGATGAGA TACGT                                                        15
```

COMPUTER-AIDED TECHNIQUES FOR ANALYZING BIOLOGICAL SEQUENCES

This application is a continuation-in-part of U.S. application Ser. No. 08/529,115, filed Sep. 15, 1995 (now issued as U.S. Pat. No. 6,040,138) and is a continuation-in-part of U.S. application Ser. No. 08/531,137, filed Oct. 16, 1995 (now U.S. Pat. No. 5,974,164), which is a continuation-in-part of U.S. application Ser. No. 08/327,525, filed Oct. 21, 1994 (now U.S. Pat. No. 5,795,716), all of which are hereby incorporated by reference for all purposes. This application is a continuation-in-part of U.S. Application No. PCT/US96/14839, filed Sep. 13, 1997, which is hereby incorporated by reference for all purposes. This application claims priority to U.S. Application No. 60/033,053, filed Dec. 12, 1996, which is hereby incorporated by reference for all purposes.

GOVERNMENT RIGHTS NOTICE

Portions of the material in this specification arose under the cooperative agreement 70NANB5H1031 between Affymetrix, Inc. and the Department of Commerce through the National Institute of Standards and Technology.

COPYRIGHT NOTICE

A portion of the disclosure of this patent document contains material which is subject to copyright protection. The copyright owner has no objection to the xerographic reproduction by anyone of the patent document or the patent disclosure in exactly the form it appears in the Patent and Trademark Office patent file or records, but otherwise reserves all copyright rights whatsoever.

BACKGROUND OF THE INVENTION

The present invention relates to the field of computer systems. More specifically, the present invention relates to computer systems for analyzing biological sequences such as nucleic acid sequences.

Devices and computer systems for forming an using arrays of materials on a substrate are known. For example, PCT application WO92/10588, incorporated herein by reference for all purposes, describes techniques for sequencing or sequence checking nucleic acids and other materials. Arrays for performing these operations may be formed in arrays according to the methods of, for example, the pioneering techniques disclosed in U.S. Pat. No. 5,143,854 and U.S. patent application Ser. No. 08/249,188 (now U.S. Pat. No. 5,571,639), both incorporated herein by reference for all purposes.

According to one aspect of the techniques described therein, an array of nucleic acid probes is fabricated at known locations on a substrate or chip. A fluorescently labeled nucleic acid is then brought into contact with the chip and a scanner generates an image file (which is processed into a cell file) indicating the locations where the labeled nucleic acids bound to the chip. Based upon the cell file and identities of the probes at specific locations, it becomes possible to extract information such as the monomer sequence of DNA or RNA. Such systems have been used to form, for example, arrays of DNA that may be used to study and detect mutations relevant to cystic fibrosis, the P53 gene (relevant to certain cancers), HIV, and other genetic characteristics.

Innovative computer-aided techniques for base calling are disclosed in U.S. patent application Ser. No. 08/53 1,137 (now U.S. Pat. No. 5,974,164), Ser. No. 08/528,656 (now U.S. Pat. No. 5,733,729), and Ser. No. 08/618,834 which are all hereby incorporated by reference for all purposes. However, improved computer systems and methods are still needed to evaluate, analyze, and process the vast amount of information now used and made available by these pioneering technologies.

Additionally, there is a need for improved computer-aided techniques for monitoring gene expression. Many disease states are characterized by differences in the expression levels of various genes either through changes in the copy number of the genetic DNA or through changes in levels of transcription (e.g., through control of initiation, provision of RNA precursors, RNA processing, etc.) of particular genes. For example, losses and gains of genetic material play an important role in malignant transformation and progression. Furthermore, changes in the expression (transciption) levels of particular genes (e.g., oncogenes or tumor suppressors), serve as signposts for the presence and progression of various cancers.

Similarly, control of the cell cycle and cell development, as well as diseases, are characterized by the variations in the transcription levels of particular genes. Thus, for example, a viral infection is often characterized by the elevated expression of genes of the particular virus. For example, outbreaks of Herpes simplex, Epstein-Barr virus infections (e.g., infectious mononucleosis), cytomegalovirus, Varicella-zoster virus infections, parvovirus infections, human papillomavirus infections, etc. are all characterized by elevated expression of various genes present in the respective virus. Detection of elevated expression levels of characteristic viral genes provides an effective diagnostic of the disease state. In particular, viruses such as herpes simplex, enter quiescent states for periods of time only to erupt in brief periods of rapid replication. Detection of expression levels of characteristic viral genes allows detection of such active proliferative (and presumably infective) states.

SUMMARY OF THE INVENTION

The present invention provides innovative systems and methods for analyzing biological sequences such as nucleic acid sequences. The computer system may analyze hybridization intensities indicating hybridization affinity between nucleic acid probes and a sample nucleic acid sequence in order to call bases in the sample sequence. Multiple base calls may be combined to form a single base call. Additionally, the computer system may analyze hybridization intensities in order to monitor gene expression or the change in gene expression as compared to a baseline.

According to one aspect of the invention, a computer-implemented method of calling an unknown base in a sample nucleic acid sequence comprises the steps of: receiving hybridization intensities for a plurality of sets of nucleic acid probes, each hybridization intensity indicating a hybridization affinity between a nucleic acid probe and the sample nucleic acid sequence; computing a base call for the unknown base for each set of probes; and computing a single base call for the plurality of sets of probes according to the base call for the unknown base which occurs most often for the plurality of sets of probes. Typically, the single base call is displayed on a screen display and a user is afforded the opportunity to display or not display the base cases from which the single base call is derived.

According to another aspect of the invention, a method of dynamically changing parameters for a computer-implemented base calling procedure comprises the steps of: generating base calls for at least a portion of a sample nucleic acid sequence utilizing the base calling procedure, the base calling procedure including a parameter that is changeable by a user; displaying the base calls for the at least a portion of a sample nucleic acid sequence; displaying the parameter of the base calling procedure; receiving input from the user specifying a new value for the parameter of the base calling procedure; generating updated base calls for the at least a portion of a sample nucleic acid sequence utilizing the base calling procedure and the new value for the parameter; and displaying the updated base calls for the at least a portion of a sample nucleic acid sequence. Typically the user-changeable parameter is a constant, threshold, or range.

According to another aspect of the invention, a computer-implemented method of monitoring expression of a gene in a sample nucleic acid sequence comprises the steps of: inputting a plurality of hybridization intensities of pairs of perfect match and mismatch probes, the perfect match probes being perfectly complementary to the gene and the mismatch probes having at least one base mismatch with the gene, and the hybridization intensities indicating hybridization infinity between the perfect match and mismatch probes and the sample nucleic acid sequence; comparing the hybridization intensities of each pair of perfect match probes; and generating a gene expression call of the sample nucleic acid sequence. In preferred embodiments, the expression call is denoted as expressed, marginal, or absent.

According to another aspect of the invention, a computer-implemented method of monitoring change in expression of a gene in a sample nucleic acid sequence comprises the steps of: inputting a plurality of hybridization intensities of pairs of perfect match and mismatch probes, the perfect match probes being perfectly complementary to the gene and the mismatch probes having at least one base mismatch with the gene, and the hybridization intensities indicating hybridization infinity between the perfect match and mismatch probes and the sample nucleic acid sequence; comparing the hybridization intensities of each pair of perfect match probes in order to generate a gene expression level of the sample nucleic acid sequence; and determining a change in expression by comparing the gene expression level to a baseline gene expression level. The change in expression may be displayed as a graph on the display screen.

A further understanding of the nature and advantages of the inventions herein may be realized by reference to the remaining portions of the specification and the attached drawings.

BRIEF DESCRIPTION OF THE DRAWINGS

FIG. 6 illustrates conceptually the binding of nucleic acid probes on chips to a labeled target;

FIG. 7 illustrates nucleic acid probes arranged in lanes on a chip (SEQ ID NO:1);

FIG. 8 illustrates a hybridization pattern of a target on a chip with a reference sequence as in FIG. 7 (SEQ ID NO:1);

FIGS. 21A and 21B show screen displays illustrating the analysis of a selected gene;

FIGS. 27A and 27B show screen displays illustrating the monitoring of the change of gene expression between experiments.

DESCRIPTION OF PREFERRED EMBODIMENTS

General

The present invention provides innovative methods of identifying nucleotides (i.e., base calling) in sample nucleic acid sequences and monitoring gene expression. In the description that follows, the invention will be described in reference to preferred embodiments. However, the description is provided for purposes of illustration and not for limiting the spirit and scope of the invention.

Figure 1:
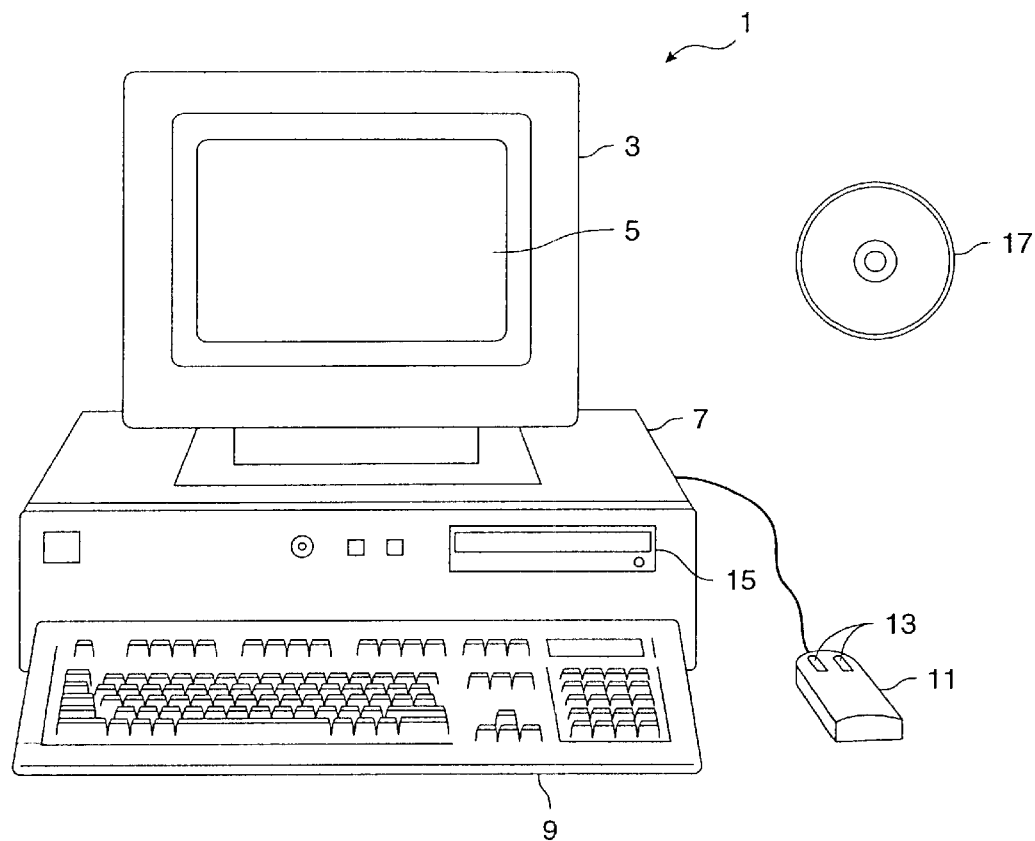
FIG. 1 illustrates an example of a computer system that may be used to execute software embodiments of the present invention.

FIG. 1 illustrates an example of a computer system that may be used to execute software embodiments of the present invention. FIG. 1 shows a computer system 1 which includes a monitor 3, screen 5, cabinet 7, keyboard 9, and mouse 11. Mouse 11 may have one or more buttons such as mouse buttons 13. Cabinet 7 houses a CD-ROM drive 15 and a hard drive (not shown) that may be utilized to store and retrieve software programs including computer code incorporating the present invention. Although a CD-ROM 17 is shown as the computer readable medium, other computer readable media including floppy disks, DRAM, hard drives, flash memory, tape, and the like may be utilized. Cabinet 7 also houses familiar computer components (not shown) such as a processor, memory, and the like.

Figure 2:
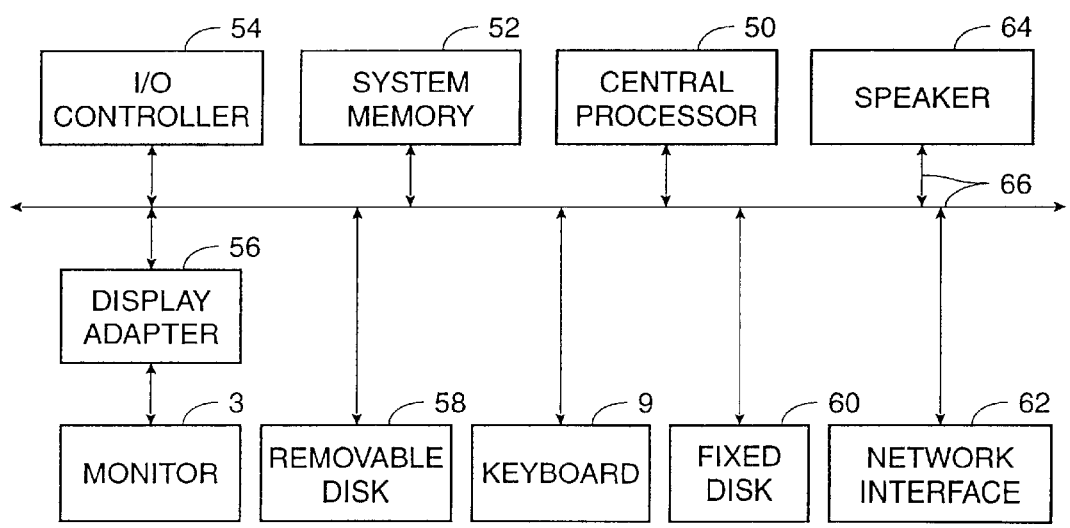
FIG. 2 shows a system block diagram of a typical computer system.

FIG. 2 shows a system block diagram of computer system 1 used to execute software embodiments of the present invention. As in FIG. 1, computer system 1 includes monitor 3 and keyboard 9. Computer system 1 further includes subsystems such as a central processor 50, system memory 52, I/O controller 54, display adapter 56, removable disk 58, fixed disk 60, network interface 62, and speaker 64. Removable disk 58 is representative of removable computer readable media like floppies, tape, CD-ROM, removable hard drive, flash memory, and the like. Fixed disk 60 is representative of an internal hard drive or the like. Other computer systems suitable for use with the present invention may include additional or fewer subsystems. For example, another computer system could include more than one processor 50 (i.e., a multi-processor system) or memory cache.

Arrows such as 66 represent the system bus architecture of computer system 1. However, these arrows are illustrative of any interconnection scheme serving to link the subsystems. For example, display adapter 56 may be connected to central processor 50 through a local bus or the system may include a memory cache. Computer system 1 shown in FIG. 2 is but an example of a computer system suitable for use with the present invention. Other configurations of subsystems suitable for use with the present invention will be readily apparent to one of ordinary skill in the art. In one embodiment, the computer system is a workstation from Sun Microsystems.

The VLSIPS™ technology provides methods of making very large arrays of oligonucleotide probes on very small chips. See U.S. Pat. No. 5,143,854 and PCT patent publication Nos. WO 90/15070 and 92/10092, each of which is hereby incorporated by reference for all purposes. The oligonucleotide probes on the chip are used to detect complementary nucleic acid sequences in a sample nucleic acid of interest (the "target" nucleic acid).

The present invention provides methods of analyzing hybridization intensity files for a chip containing hybridized nucleic acid probes. In a representative embodiment, the files represent fluorescence data from a biological array, but the files may also represent other data such as radioactive intensity data. Therefore, the present invention is not limited to analyzing fluorescent measurements of hybridizations but may be readily utilized to analyze other measurements of hybridization.

For purposes of illustration, the present invention is described as being part of a computer system that designs a chip mask, synthesizes the probes on the chip, labels the nucleic acids, and scans the hybridized nucleic acid probes. Such a system is fully described in U.S. patent application Ser. No. 08/249,188 (now U.S. Pat. No. 5,571,639) which is hereby incorporated by reference for all purposes. However, the present invention may be used separately from the overall system for analyzing data generated by such systems, such as at remote locations.

Figure 3:
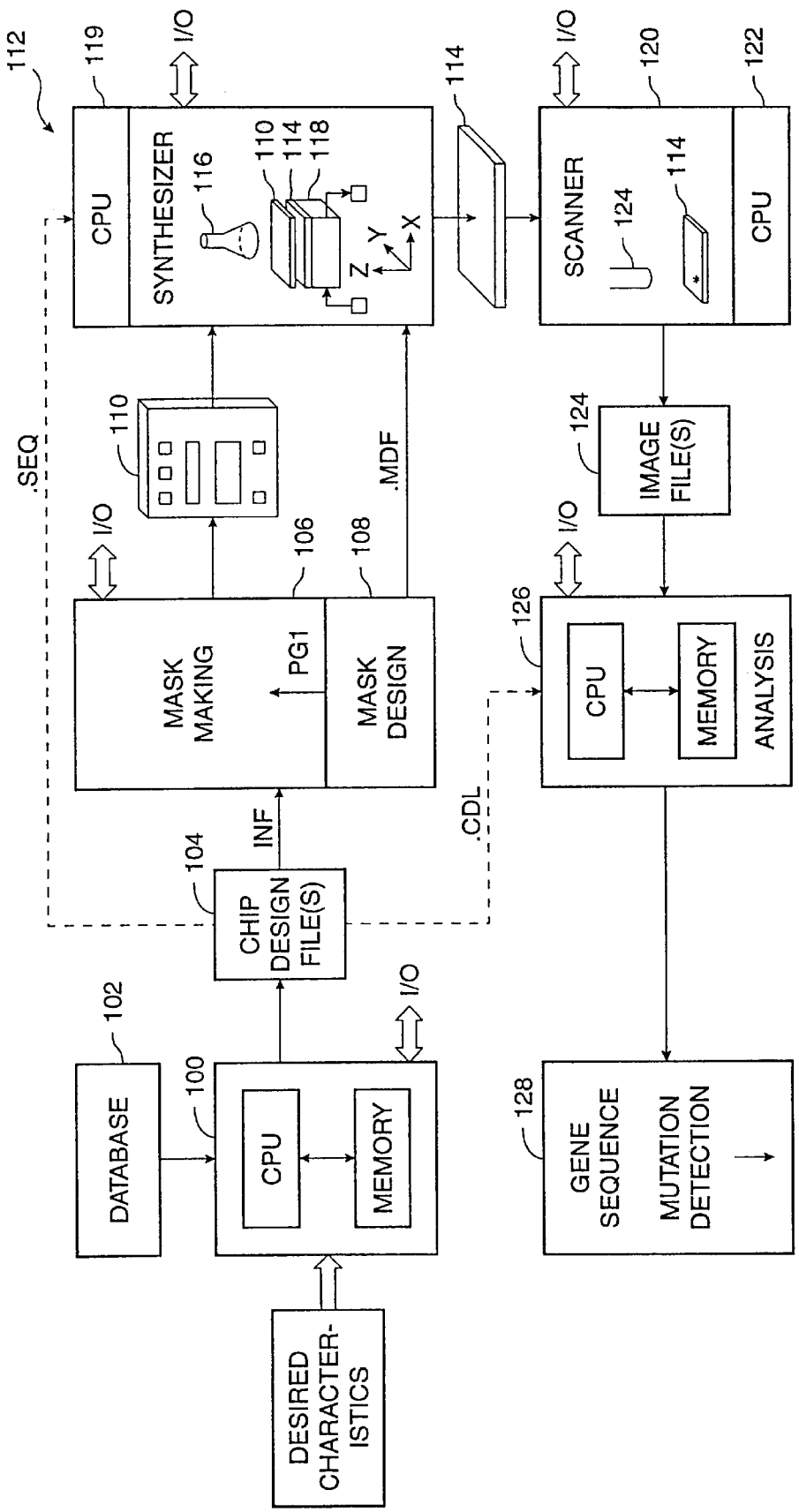
FIG. 3 illustrates an overall system for forming and analyzing arrays of biological materials such as DNA or RNA.

FIG. 3 illustrates a computerized system for forming and analyzing arrays of biological materials such as RNA or DNA. A computer 100 is used to design arrays of biological polymers such as RNA or DNA. The computer 100 may be, for example, an appropriately programmed IBM personal computer compatible running Windows NT including appropriate memory and a CPU as shown in FIGS. 1 and 2. The computer system 100 obtains inputs from a user regarding characteristics of a gene of interest, and other inputs regarding the desired features of the array. Optionally, the computer system may obtain information regarding a specific genetic sequence of interest from an external or internal database 102 such as GenBank. The output of the computer system 100 is a set of chip design computer files 104 in the form of, for example, a switch matrix, as described in PCT application WO 92/10092, and other associated computer files.

The chip design files are provided to a system 106 that designs the lithographic masks used in the fabrication of arrays of molecules such as DNA. The system or process 106 may include the hardware necessary to manufacture masks 110 and also the necessary computer hardware and software 108 necessary to lay the mask patterns out on the mask in an efficient manner. As with the other features in FIG. 3, such equipment may or may not be located at the same physical site, but is shown together for ease of illustration in FIG. 3. The system 106 generates masks 110 or other synthesis patterns such as chrome-on-glass masks for use in the fabrication of polymer arrays.

The masks 110, as well as selected information relating to the design of the chips from system 100, are used in a synthesis system 112. Synthesis system 112 includes the necessary hardware and software used to fabricate arrays of polymers on a substrate or chip 114. For example, synthesizer 112 includes a light source 116 and a chemical flow cell 118 on which the substrate or chip 114 is placed. Mask 110 is placed between the light source and the substrate/chip, and the two are translated relative to each other at appropriate times for deprotection of selected regions of the chip. Selected chemical reagents are directed through flow cell 118 for coupling to deprotected regions, as well as for washing and other operations. All operations are preferably directed by an appropriately programmed computer 119, which may or may not be the same computer as the computer(s) used in mask design and mask making.

The substrates fabricated by synthesis system 112 are optionally diced into smaller chips and exposed to marked targets. The targets may or may not be complementary to one or more of the molecules on the substrate. The targets are marked with a label such as a fluorescein label (indicated by an asterisk in FIG. 3) and placed in scanning system 120. Scanning system 120 again operates under the direction of an appropriately programmed digital computer 122, which also may or may not be the same computer as the computers used in synthesis, mask making, and mask design. The scanner 120 includes a detection device 124 such as a confocal microscope or CCD (charge-coupled device) that is used to detect the location where labeled target (*) has bound to the substrate. The output of scanner 120 is an image file(s) 124 indicating, in the case of fluorescein labeled target, the fluorescence intensity (photon counts or other related measurements, such as voltage) as a function of position on the substrate. Since higher photon counts will be observed where the labeled target has bound more strongly to the array of polymers, and since the monomer sequence of the polymers on the substrate is known as a function of position, it becomes possible to determine the sequence(s) of polymer(s) on the substrate that are complementary to the target.

The image file 124 is provided as input to an analysis system 126 that incorporates the visualization and analysis methods of the present invention. Again, the analysis system may be any one of a wide variety of computer system(s). The present invention provides various methods of analyzing the chip design files and the image files, providing appropriate output 128. The present invention may further be used to identify specific mutations in a target such as DNA or RNA.

Figure 4:
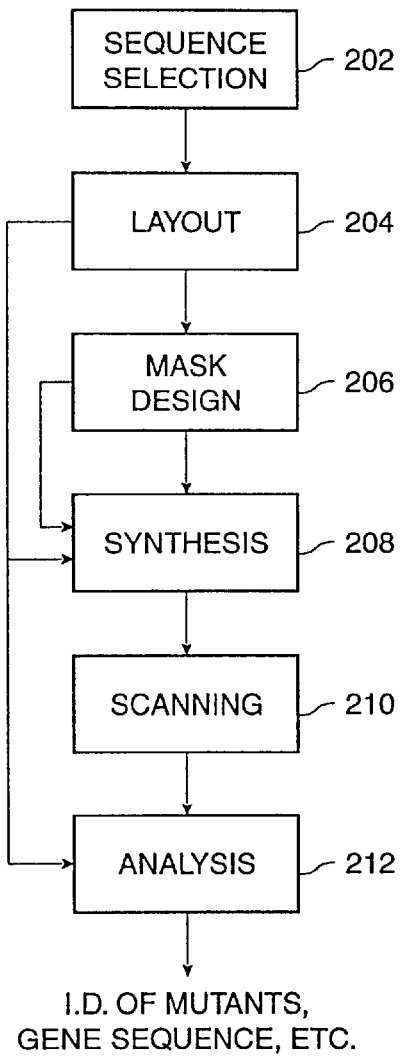
FIG. 4 is an illustration of an embodiment of software for the overall system.

FIG. 4 provides a simplified illustration of the overall software system used in the operation of one embodiment of the invention. As shown in FIG. 4, the system first identifies the genetic sequence(s) or targets that would be of interest in a particular analysis at step 202. The sequences of interest may, for example, be normal or mutant portions of a gene, genes that identify heredity, or provide forensic information. Sequence selection may be provided via manual input of text files or may be from external sources such as GenBank. At step 204 the system evaluates the gene to determine or assist the user in determining which probes would be desirable on the chip, and provides an appropriate "layout" on the chip for the probes.

The chip usually includes probes that are complementary to a reference nucleic acid sequence which has a known sequence. A wild-type probe is a probe that will ideally hybridize with the reference sequence and thus a wild-type gene (also called the chip wild-type) would ideally hybridize with wild-type probes on the chip. The target sequence is substantially similar to the reference sequence except for the presence of mutations, insertions, deletions, and the like. The layout implements desired characteristics such as arrangement on the chip that permits "reading" of genetic sequence and/or minimization of edge effects, ease of synthesis, and the like.

Figure 5:
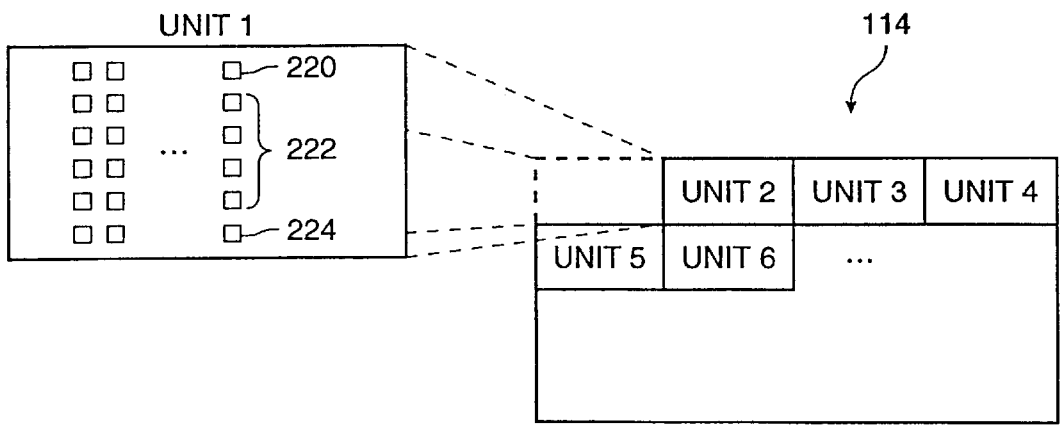
FIG. 5 illustrates the global layout of a chip formed in the overall system.

FIG. 5 illustrates the global layout of a chip. Chip 114 is composed of multiple units where each unit may contain different tilings for the wild-type sequence or multiple wild-type sequences. Unit 1 is shown in greater detail and shows that each unit is composed of multiple cells which are areas on the chip that may contain probes. Conceptually, each unit includes multiple sets of related cells. As used herein, the term cell refers to a region on a substrate that contains many copies of a molecule or molecules (e.g., nucleic acid probes).

Each unit is composed of multiple cells that may be placed in rows (or "lanes") and columns. In one embodiment, a set of five related cells includes the following: a wild-type cell 220, "mutation" cells 222, and a "blank" cell 224. Cell 220 contains a wild-type probe that is the complement of a portion of the wild-type sequence. Cells 222 contain "mutation" probes for the wild-type sequence. For example, if the wild-type probe is 3'-ACGT, the probes 3'-ACAT, 3'-ACCT, 3'-ACGT, and 3'-ACTT may be the "mutation" probes. Cell 224 is the "blank" cell because it contains no probes (also called the "blank" probe). As the blank cell contains no probes, labeled targets should not bind to the chip in this area. Thus, the blank cell provides an area that can be used to measure the background intensity.

Again referring to FIG. 4, at step 206 the masks for the synthesis are designed. At step 208 the software utilizes the mask design and layout information to make the DNA or other polymer chips. This software 208 will control, among other things, relative translation of a substrate and the mask, the flow of desired reagents through a flow cell, the synthesis temperature of the flow cell, and other parameters. At step 210, another piece of software is used in scanning a chip thus synthesized and exposed to a labeled target. The software controls the scanning of the chip, and stores the data thus obtained in a file that may later be utilized to extract sequence information.

At step 212 a computer system utilizes the layout information and the fluorescence information to evaluate the hybridized nucleic acid probes on the chip. Among the important pieces of information obtained from DNA chips are the identification of mutant targets and determination of genetic sequence of a particular target.

FIG. 6 illustrates the binding of a particular target DNA to an array of DNA probes 114. As shown in this simple example, the following probes are formed in the array (only one probe is shown for the wild-type probe):

```
3'-AGAACGT
  AGACCGT
  AGAGCGT
  AGATCGT
  .
  .
  .
```

As shown, the set of probes differ by only one base, a single base mismatch at an interrogation position, so the probes are designed to determine the identity of the base at that location in the nucleic acid sequence. Accordingly, when used herein a unit will refer to multiple sets of related probes, where each set includes probes that differ by a single base mismatch at an interrogation position.

When a fluorescein-labeled (or other marked) target with the sequence 5'-TCTTGCA is exposed to the array, it is complementary only to the probe 3'-AGAACGT, and fluorescein will be primarily found on the surface of the chip where 3'-AGAACGT is located. Thus, for each set of probes that differ by only one base, the image file will contain four fluorescence intensities, one for each probe. Each fluorescence intensity can therefore be associated with the nucleotide or base of each probe that is different from the other probes. Additionally, the image file will contain a "blank" cell which can be used as the fluorescence intensity of the background. By analyzing the five fluorescence intensities associated with a specific base location, it becomes possible to extract sequence information from such arrays using the methods of the invention disclosed herein.

FIG. 7 illustrates probes arranged in lanes on a chip. A reference sequence (or chip wild-type sequence) is shown with five interrogation positions marked with number subscripts. An interrogation position is oftentimes a base position in the reference sequence where the target sequence may contain a mutation or otherwise differ from the reference sequence. The chip may contain five probe cells that correspond to each interrogation position. Each probe cell contains a set of probes that have a common base at the interrogation position. For example, at the first interrogation position, $I_1$, the reference sequence has a base T. The wild-type probe for this interrogation position is 3'-TGAC where the base A in the probe is complementary to the base at the interrogation position in the reference sequence.

Similarly, there are four "mutant" probe cells for the first interrogation position, $I_1$. The four mutant probes are 3'-TGAC, 3'-TGCC, 3'-TGGC, and 3'-TGTC. Each of the four mutant probes vary by a single base at the interrogation position. As shown, the wild-type and mutant probes are arranged in lanes on the chip. One of the mutant probes (in this case 3'-TGAC) is identical to the wild-type probe and therefore does not evidence a mutation. However, the redundancy gives a visual indication of mutations as will be seen in FIG. 8.

Still referring to FIG. 7, the chip contains wild-type and mutant probes for each of the other interrogation positions $I_2$–$I_5$. In each case, the wild-type probe is equivalent to one of the mutant probes.

FIG. 8 illustrates a hybridization pattern of a target on a chip with a reference sequence as in FIG. 7. The reference sequence is shown along the top of the chip for comparison. The chip includes a WT-lane (wild-type), an A-lane, a C-lane, a G-lane, and a T-lane (or U). Each lane is a row of cells containing probes. The cells in the WT-lane contain probes that are complementary to the reference sequence. The cells in the A-, C-, G-, and T-lanes contain probes that are complementary to the reference sequence except that the named base is at the interrogation position.

In one embodiment, the hybridization of probes in a cell is determined by the fluorescent intensity (e.g., photon counts) of the cell resulting from the binding of marked target sequences. The fluorescent intensity may vary greatly among cells. For simplicity, FIG. 8 shows a high degree of hybridization by a cell containing a darkened area. The WT-lane allows a simple visual indication that there is a mutation at interrogation position $I_4$ because the wild-type cell is not dark at that position. The cell in the C-lane is darkened which indicates that the mutation is from T->G (mutant probe cells are complementary so the C-cell indicates a G mutation). In a preferred embodiment, the WT-Lane is not utilized so four cells (not including any "blank" cell) are utilized to call a base at an interrogation position.

In practice, the fluorescent intensities of cells near an interrogation position having a mutation are relatively dark creating "dark regions" around a mutation. The lower fluorescent intensities result because the cells at interrogation positions near a mutation do not contain probes that are perfectly complementary to the target sequence; thus, the hybridization of these probes with the target sequence is lower. For example, the relative intensity of the cells at interrogation positions $I_3$ and $I_5$ may be relatively low because none of the probes therein are complementary to the target sequence. Although the lower fluorescent intensities reduce the resolution of the data, the methods of the present invention provide highly accurate base calling within the dark regions around a mutation and are able to identify other mutations within these regions.

Figure 9:
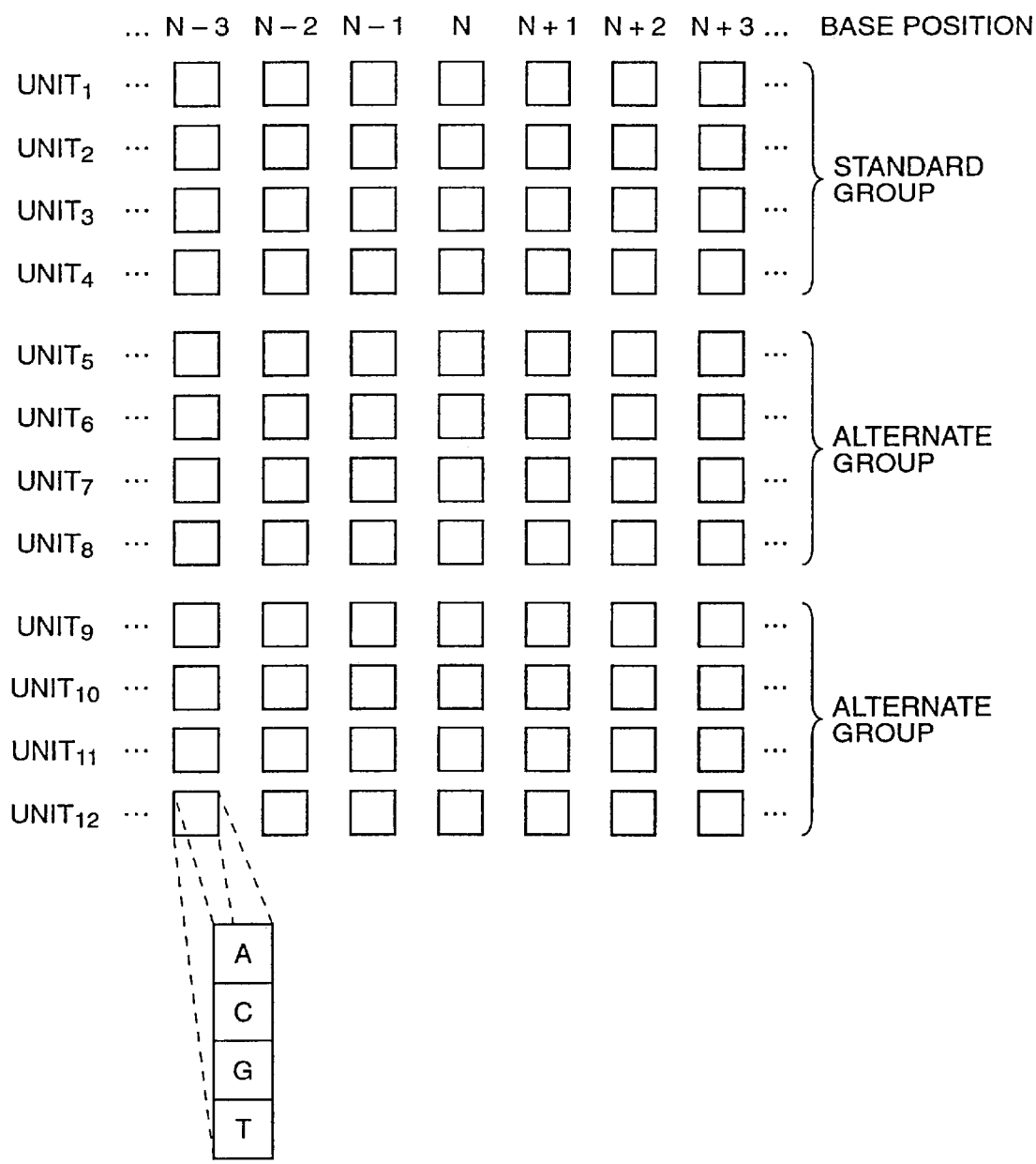
FIG. 9 illustrates standard and alternate tilings.

FIG. 9 illustrates standard and alternate tilings on a chip. As shown, the chip includes twelve units (units$_{1-12}$). Units$_{1-4}$ are tiled (i.e., designed and synthesized on the chip) to include probes complementary to the same reference sequence. For identification purposes, this group of units will be called the standard group. In general, base calls for the target sequence will be performed utilizing the standard group unless the invention determines that another group or groups should be utilized.

Units$_{5-8}$ are tiled to include probes complementary to the same reference sequence, but a reference sequence that differs from the reference sequence for the standard group. This group of units will be called an alternate group. Units$_{9-12}$ comprises another alternate group that are based on a reference sequence that is different from the reference sequences of the standard and first alternate groups. Although the reference sequences are different, they are often quite similar. For example, the reference sequences may be slightly different mutations of HIV. Embodiments of the present invention evaluate and utilize information from tilings based on reference sequences that would typically not be used in base calling the target sequence.

The units within a group may include identical probes, probes of different structure, probes from the same or different chips, and the like. For example, one unit may include 5-mer probes with the interrogation position at the third position in probes. Another unit may include 10-mer probes with an interrogation position at the sixth position. Additionally, these units may have been tiled on the same or different chips.

The expanded section at the bottom left portion of FIG. 9 illustrates that each block of a unit typically includes four cells, denoted A, C, G, and T. The base designations specify which base is at the interrogation position of each probe within the cell. Typically, there are hundreds or thousands of identical nucleic probes within each cell.

Although in preferred embodiments the cells may be arranged adjacent to each other in sequential order along the reference sequence, there is no requirement that the cells be in any particular location as long as the location on the chip is determinable. Additionally, although it may be beneficial to synthesize the different groups on a single chip for consistency of experiments, the methods of the present invention may be advantageously utilized with data from different tilings on different chips.

Analyzing Target Sequences

Figure 10:
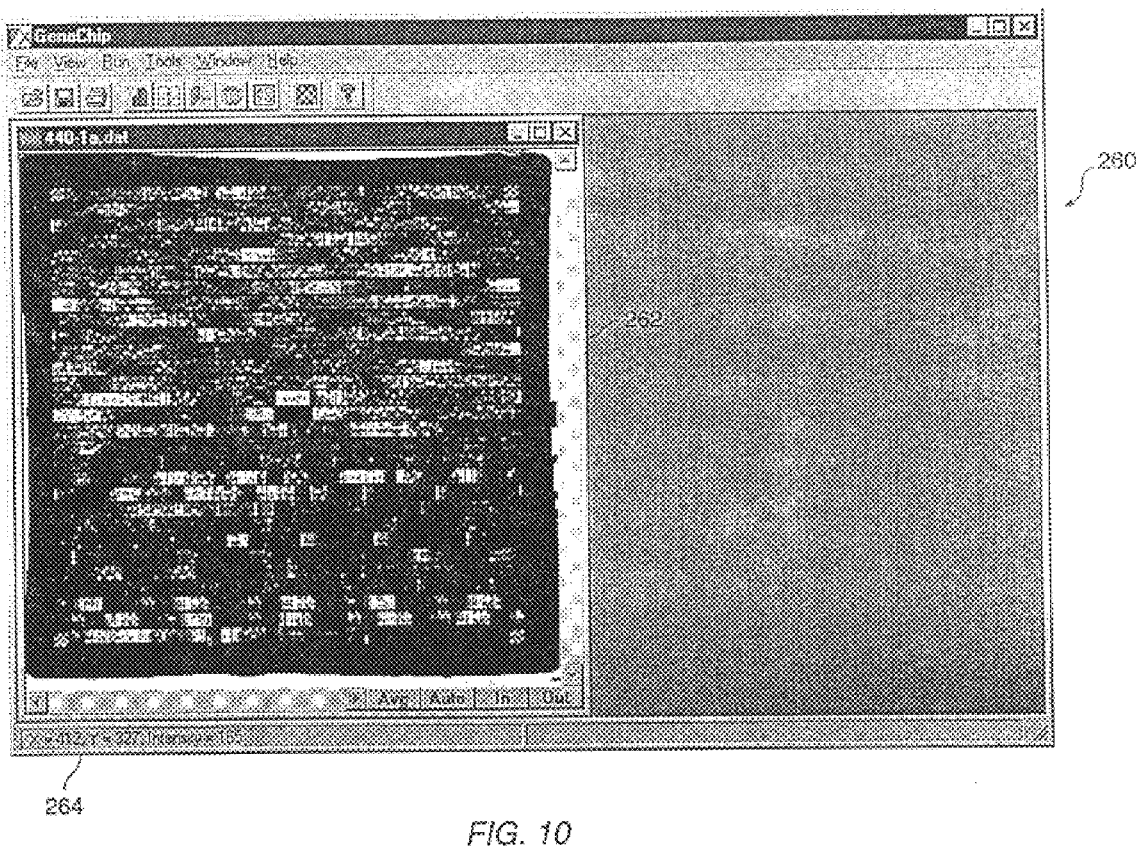
FIG. 10 shows a screen display of hybridization intensities from a chip.

FIG. 10 shows a screen display of hybridization intensities from a chip. During analysis, the system receives an image file including the scanned image of the hybridized chip. In a preferred embodiment, the image file shows fluorescent intensities and locations that labeled target nucleic acid sequences or fragments bound to the chip.

A screen display 260 utilizes the common windowing graphical user interface. The user may select to display the image file for inspection. After the user selects the image file to be displayed, a window 262 is displayed that includes the image file. The image file shown includes multiple rows of A-, C-, G-, and T-lanes.

As the user moves the cursor over the displayed image file, a status bar 264 indicates the X and Y position of the cursor and the fluorescent intensity at that position. Additionally, the user is able to utilize the pointing device to select a rectangular area of the image file in order to manipulate the sub-image. For example, the user may magnify the subimage so that the individual cells may be seen more clearly. Additionally, the user may adjust the contrast of the intensities to bring to light some differences in hybridization intensity that is not apparent at the current contrast setting.

Figure 11:
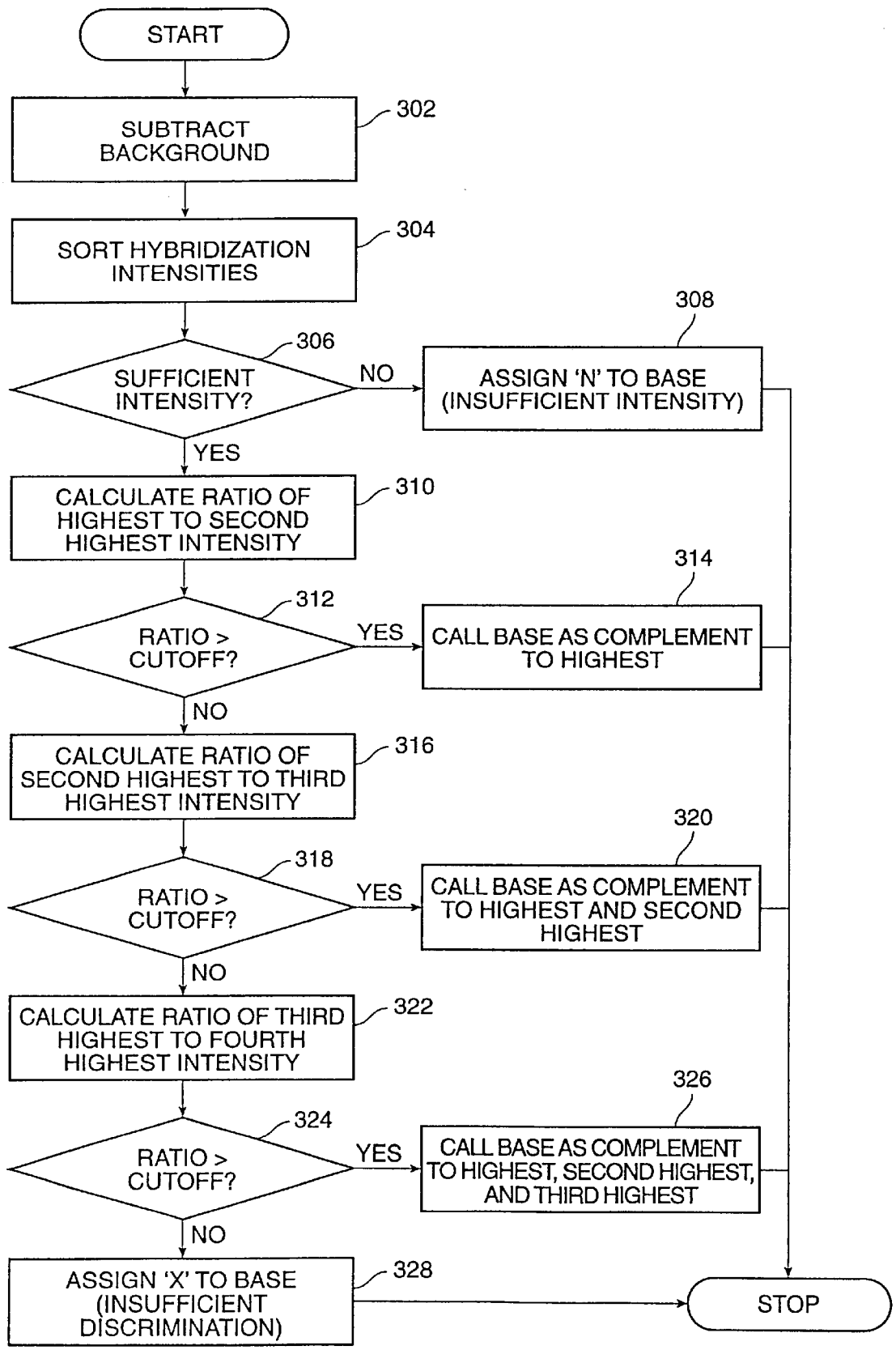
FIG. 11 is a flowchart of a process of computing a base call from hybridization intensities of related probes.

FIG. 11 is a flowchart of a process of computing a base call from hybridization intensities of related probes. When used herein, "related probes" are probes that differ by a nucleotide base at an interrogation position. Although typically the probes are identical except at the interrogation position, the probes may differ at other base positions as well. Accordingly, the related probes differ by at least one base.

At step 302 the hybridization intensities of the four related probes are adjusted by subtracting the background or "blank" cell intensity. Preferably, if a hybridization intensity is then less than or equal to zero, the hybridization intensity is set equal to a small positive number to prevent division by zero or negative numbers in future calculations.

At step 304, the hybridization intensities are sorted by intensity. The highest intensity is then compared to a predetermined background difference cutoff at step 306. The background difference cutoff is a number that specifies the hybridization intensity the highest intensity probe must be over the background intensity in order to correctly call the unknown base. Thus, the background adjusted base intensity must be greater than the background difference cutoff or the unknown base is deemed to be not accurately callable.

If the highest hybridization intensity of the related probes is not greater than the background difference cutoff, the unknown base is assigned the code 'N' (insufficient intensity) as shown at step 308. Otherwise, the ratio of the highest hybridization intensity and second highest hybridization intensity is calculated as shown at step 310.

At step 312, the ratio calculated at step 310 is compared to a predetermined ratio cutoff. The ratio cutoff is a number that specifies the ratio required to identify the unknown base. In preferred embodiments, the ratio cutoff if 1.2. If the ratio is greater than the ratio cutoff, the unknown base is called according to the probe with the highest hybridization intensity. Typically, the base is called as the complement of the base at the interrogation position in the highest intensity probe as shown at step 314. Otherwise, the ratio of the second highest hybridization intensity and third highest hybridization intensity is calculated as shown at step 316.

At step 318, the ratio calculated at step 316 is compared to the ratio cutoff. If the ratio is greater than the ratio cutoff, the unknown base is called as being an ambiguity code specifying the complements of interrogation position bases of the highest hybridization intensity probe and the second highest hybridization probe as shown at step 320. Otherwise, the ratio of the third highest hybridization intensity and fourth highest hybridization intensity is calculated as shown at step 322.

At step 324, the ratio calculated at step 322 is compared to the ratio cutoff. If the ratio is greater than the ratio cutoff, the unknown base is called as being an ambiguity code specifying the complements of interrogation position bases of the highest, second highest and third highest hybridization intensity probes as shown at step 326. Otherwise, the unknown base is assigned the code 'X' (insufficient discrimination) as shown at step 328.

Figure 12:
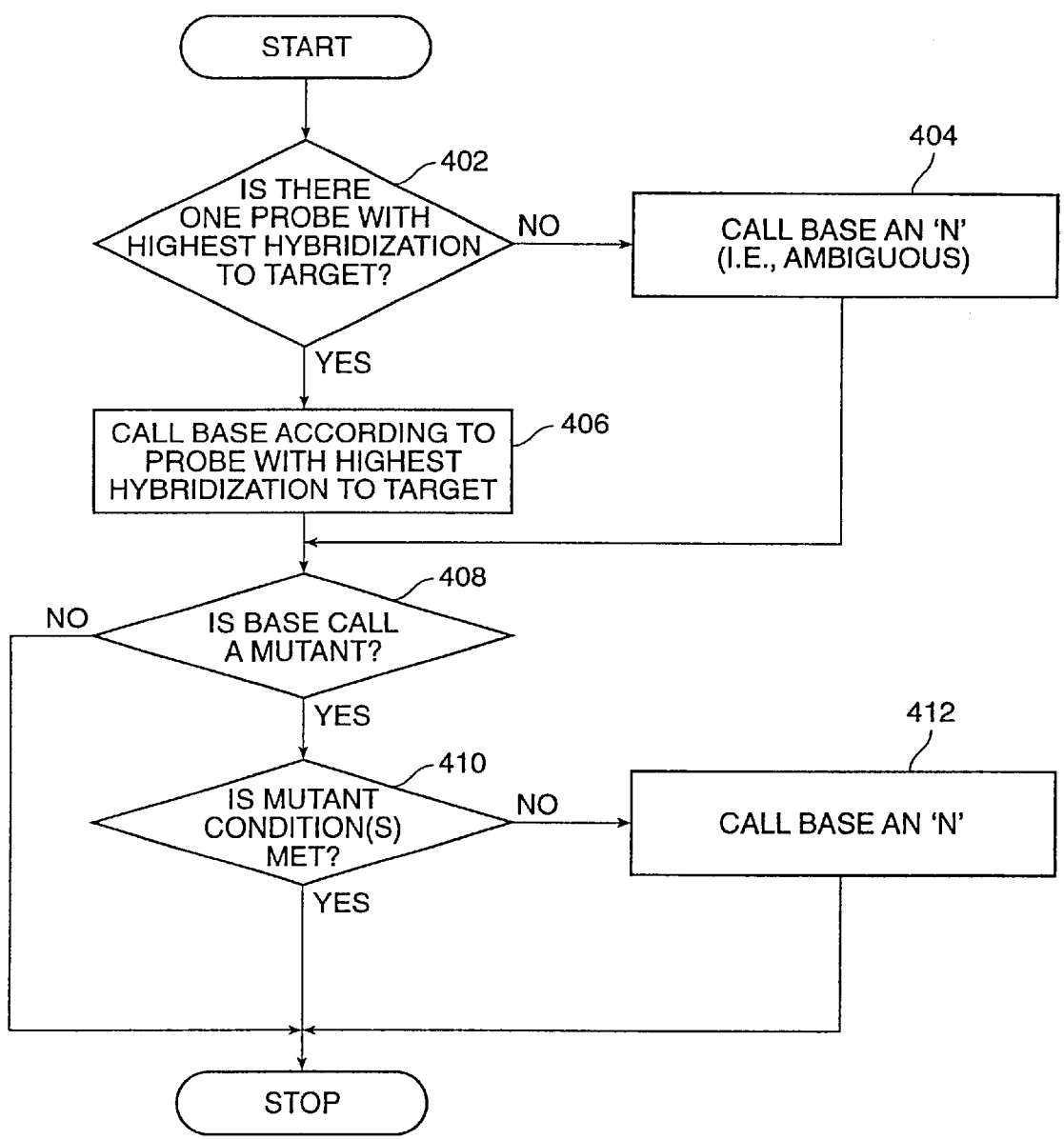
FIG. 12 is a flowchart of another process of computing a base call from hybridization intensities of related probes.

FIG. 12 is a flowchart of another process of computing a base call from hybridization intensities of related probes. The flowchart shown operates on hybridization intensities demonstrated by related probes; thus, a base call is made for the base in the target corresponding to the interrogation position in probes that differ by a single base mismatch at the interrogation position. At step 402, the system determines if there is one probe with the highest hybridization to the target sequence. If there is not, the base is called as an 'N' meaning ambiguous. For example, if two probes have the same highest intensity (i.e., there is a tie), the base would be called as 'N'.

If there is a single probe that has the highest hybridization to the target, the base is called according to that probe at step 406. Since the probes are complementary to the target sequence, the base may be called as the complementary base (C/G, A/T) to the base at the interrogation position of the probe.

At step 408, the system determines if the base call is a mutant, meaning it is different than the base in the reference sequence. If the base call is not a mutant base call, the base call has been made. Otherwise, the system determines checks to make sure certain "mutant" conditions are met at step 410 or the base is called as 'N' at step 412.

Before describing the mutant conditions for one embodiment, it may be beneficial to give labels to the hybridization intensities of the related probes. For illustration purposes "HighInt" will refer to the highest hybridization intensity, "SecondInt" will refer to the second highest hybridization intensity, "ThirdInt" will refer to the third highest hybridization intensity, and "LowInt" will refer to the lowest highest hybridization intensity.

In one embodiment, the mutant conditions include three tests that must all be met to call the base a mutant. A first test is whether the different between HighInt and SecondInt is greater than a difference cutoff. Thus, the system determines if HighInt−SecondInt is greater than a predefined value. This value should be chosen to allow mutant base calls only when the highest hybridization intensity is greater than the next highest hybridization intensity by a desired amount.

A second test is whether a first ratio is less than a first ratio cutoff. The first ratio is the following:

$$\frac{SecondInt - sqrt(ThirdInt * LowInt)}{HighInt - sqrt(ThirdInt * LowInt)}$$

The system determines if this first ratio is less than a predefined value. This value should be chosen to allow mutant base calls only when the highest hybridization intensity is a desired ratio greater than the next highest hybridization intensity even after the lowest two hybridization intensities are subtracted out.

A third test is whether a neighbor ratio is greater than a neighbor ratio cutoff. The neighbor ratio is the following:

$$\frac{HighInt_n}{HighInt_n - sqrt(HighInt_{n+1} * HighInt_{n-1})}$$

where the subscript n designates values for the base position that is being called and n+1 and n−1 represent values for adjacent base positions. Thus, the system determines if the neighbor ratio is greater than a predefined value. This value should be chosen to allow mutant base calls only when the highest hybridization intensity is a desired ratio greater than the highest hybridization intensity with the adjacent highest hybridization intensities subtracted out.

Accordingly, in a preferred embodiment, only if all of the mutant conditions are met will the base be called a mutant base. This embodiment recognizes that mutations are fairly rare so a mutant base should only be called when there is a high likelihood that there has been a mutation. If the mutant conditions are not met, the base may be called as ambiguous or as the same as the reference sequence (which statistically may be the correct base call).

Although a preferred embodiment utilizes three mutant conditions, other embodiments may use a single mutant condition (e.g., one of the conditions described above). Other embodiments may utilize other base calling methods including the ones described in the U.S. patent applications previously incorporated by reference.

Figure 13:
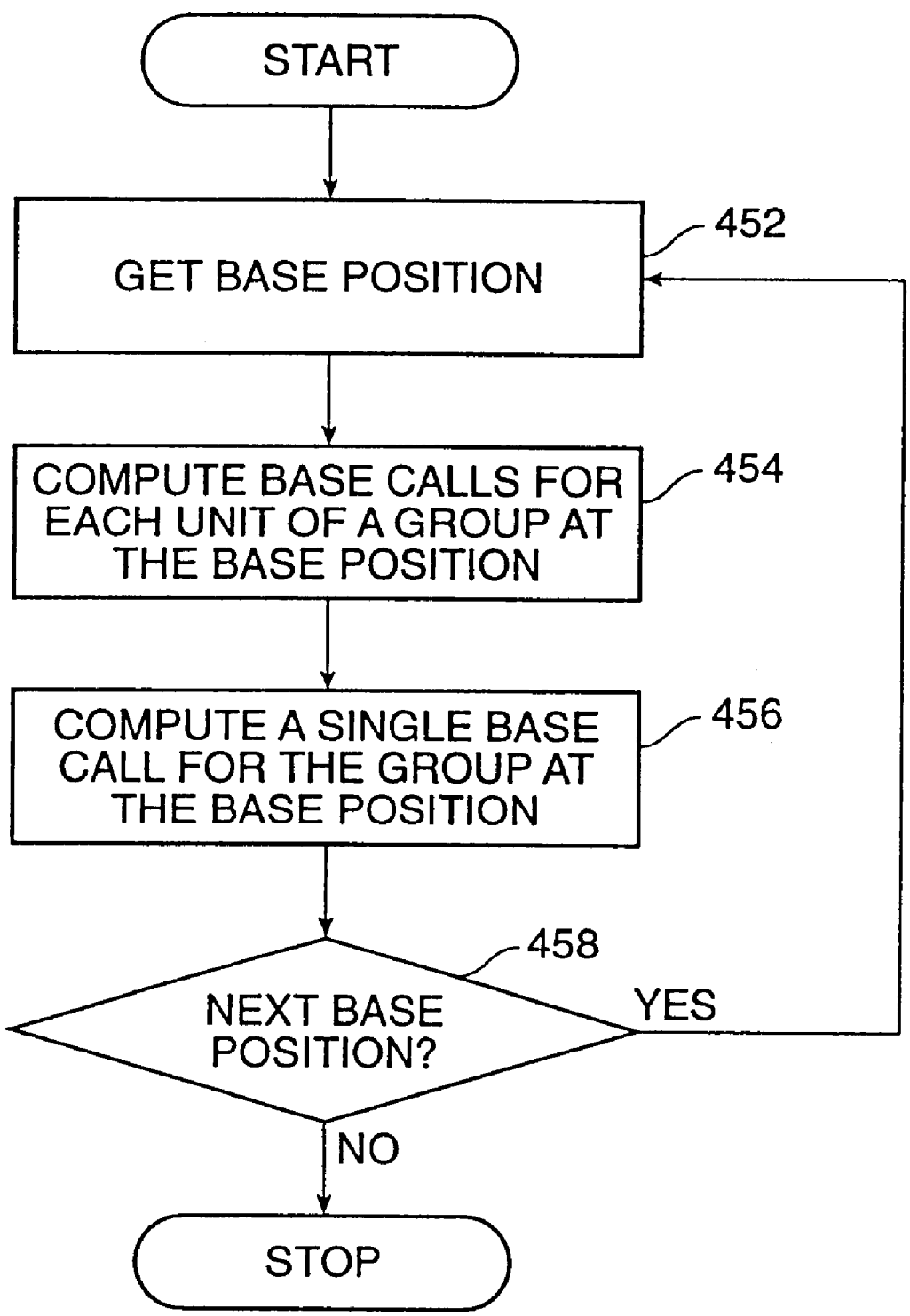
FIG. 13 is a flowchart of a process of calling bases in a group of units.

FIG. 13 is a flowchart of a process of calling bases in a group of units. As indicated earlier, a unit includes multiple sets of related cells, where the related cells include probes that differ by a single base at an interrogation position. In a typical embodiment, the system initially receives input on the hybridization intensities (e.g., from the image data file produced by a scanner that scans the hybridized chip) and the structure of the probes that correspond to the hybridization intensities. In preferred embodiments, the background intensity (e.g., intensity measured from "blank" cells or other areas of the chip without probes) are subtracted from the measured hybridization intensities. The background subtracted hybridization intensities may also be limited to have a minimum hybridization intensity of 1 (e.g., one photon count).

The hybridization intensity describes the extent of hybridization that was measured between a probe (or multiple copies of a probe) and the target sequence. As an example, the hybridization intensity may refer to the mean of the photon counts recorded from a cell, the photon counts resulting from fluorescein labeled target sequences that bound to probes in the cell.

At step 452, the system gets a base position in the target sequence to be called. The system then computes a base call for each unit of the group at step 454. Therefore, the hybridization intensities for the related cells of each unit at the base position are analyzed. With this analysis (embodiments of which were described in more detail in reference to FIGS. 11 and 12), the system computes a base call for each unit. Thus, if there are five units in the group, five base calls may be produced.

The system analyzes the base calls of the units of the group at step 456 in order to compute a base call for the group. In one embodiment, the system calls the base according to the base which is called most often by the units. For example, if there are five units and the following base calls were made for each unit:

'T'-three units
'G'-one unit
'N'-one unit

The base will be called a T since three out of five units agree. Ties may be broken by analyzing other factors like the highest average hybridization intensity of the unit or units that call each base in the tie. In a preferred embodiment, the invention utilizes the process described in FIG. 15.

At step 458, it is determined whether there is next base position to analyze. The present invention may be utilized to call all the bases of a target nucleic acid sequence so the process may, in effect, "walk" through the base positions. Additionally, the invention may be utilized to call only certain base positions (e.g., mutation positions) so the process may skip certain base positions altogether.

Figure 14:
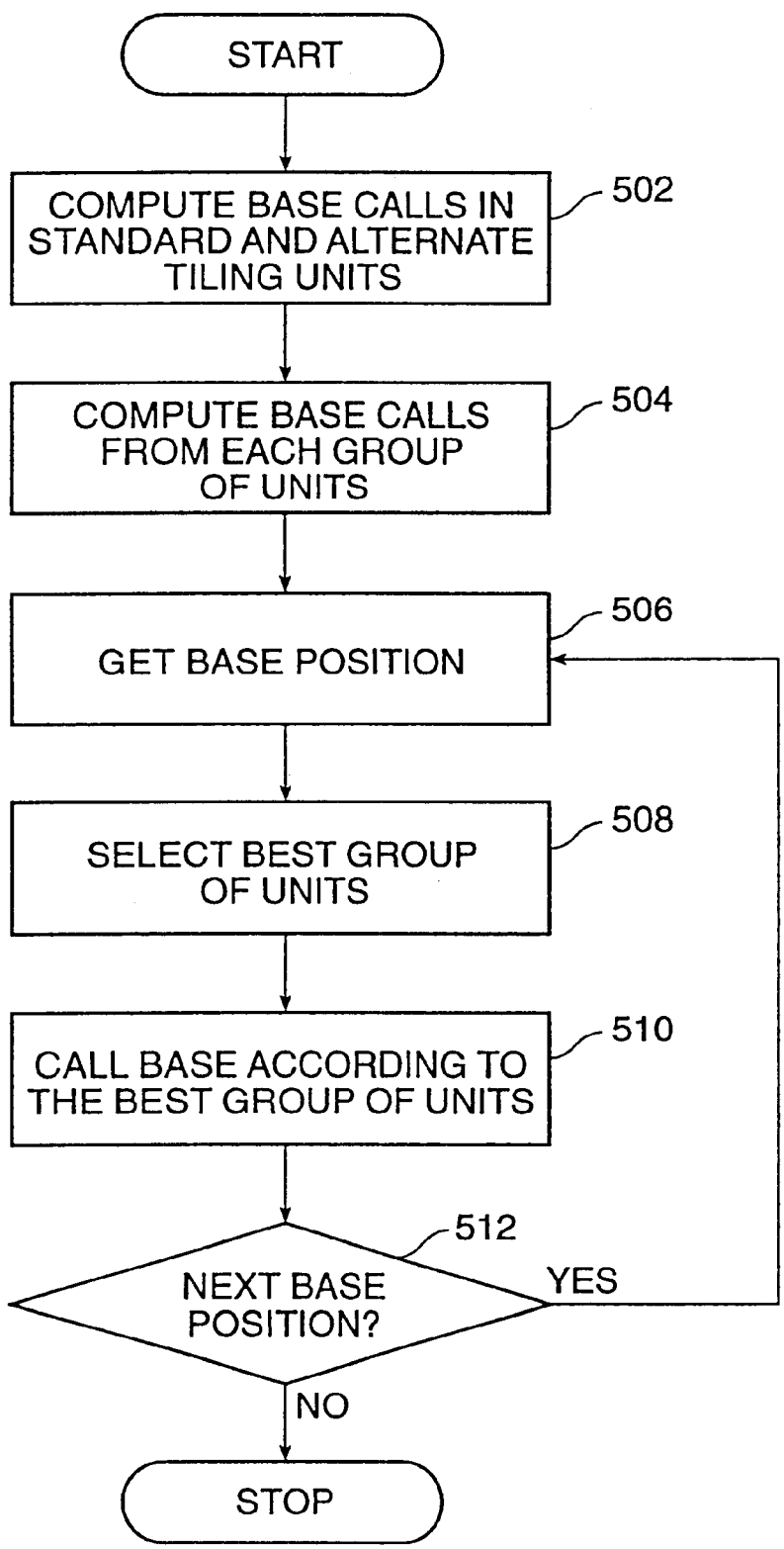
FIG. 14 is a flowchart of a process of calling bases for multiple groups of units.

FIG. 14 is a flowchart of a process of calling bases for multiple groups of units. As shown in FIG. 9, there may be multiple groups on one or more chips that are to be analyzed. The multiple groups may be tiled according to different reference sequences; however, this does not mean that all of their hybridization information may not be utilized. Typically, it is assumed that the reference sequence for the standard group is expected to be the most identical to the target sequence. However, if one of the alternate groups is determined to be more identical (i.e., better for making a base call), then that group will be used to make the base call.

At step 502, the system computes base calls in the units of the standard and alternate groups. The base calling may be done as was described in reference to FIG. 13.

The system then computes a base call for each group of units at step 504. This may be accomplished by determining the base that is called most often by the units. Alternatively, the base call for the group may be determined utilizing the process which will be described in more detail in reference to FIG. 15.

After the system has determined a base call for each group of units (both the standard and alternate tilings), the system identifies a base position at step 506. The system then determines the best group of units for this base position to be utilized to make the base call. In general, selecting the best group may involve determining which reference sequence of the groups has the fewest mismatches with the target sequence near or in a window around the interrogation position. The group of units that has the fewest mismatches near the interrogation position may have the highest likelihood of producing the most accurate base call. An embodiment of selecting the best group will be described in more detail in reference to FIG. 16.

At step 510, the system calls the base at the identified base position according to the best group of units (i.e., utilizing the base call for the group that was computed at step 504). Once the base call has been made, the system determines if there is a next base position to perform a base call. If there is another base position to be called, the system proceeds to call that base position at step 506.

Figure 15:
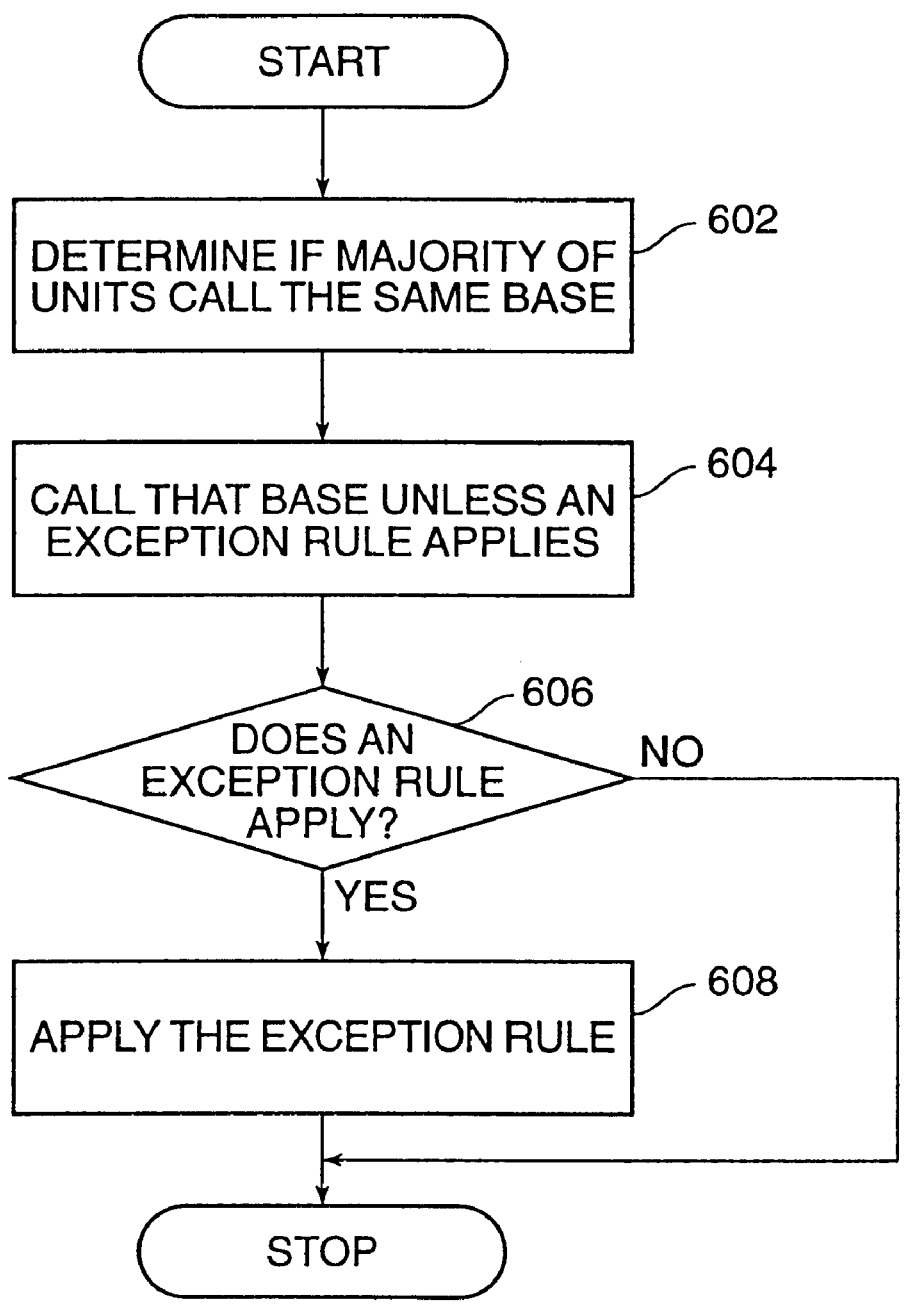
FIG. 15 is a flowchart of a process of calling a base for a group of units.

FIG. 15 is a flowchart of a process of calling a base for a group of units. At step 602, the system determines if a majority of units call the same base at the specified base position. The majority is determined upon reference to only those units that call a base (e.g., do not call as ambiguous or 'N'). For example, assume that there are seven units and the following base calls have been made for the units:

'G'-three units
'T'-one unit
'N'-four units

Since three out of four of the nonambiguous base calls are 'G', the system will initially call the base as a 'G' for the group of units. The base will be called as the majority base unless an exception rule applies at step 604.

The exception rules specify conditions which dictate what base call should be made for the group of units. These rules may include conditions that change a majority base call and may include conditions to deal with situations when there is not a base call that a majority of units call. In a preferred embodiment, the exception rules include tie breaking rules which analyze the hybridization intensity of neighboring probes (e.g., one unit calls one base and another unit calls a different base). Additionally, the exception rules specify that if three units call different bases with one of the calls being for the reference base, the system should call the base as the reference for the group of units. Other exception rules are described in the Appendix.

At step 606, the system determines if an exception rule applies. If an exception rule does apply, the rule is applied at step 608.

Figure 16:
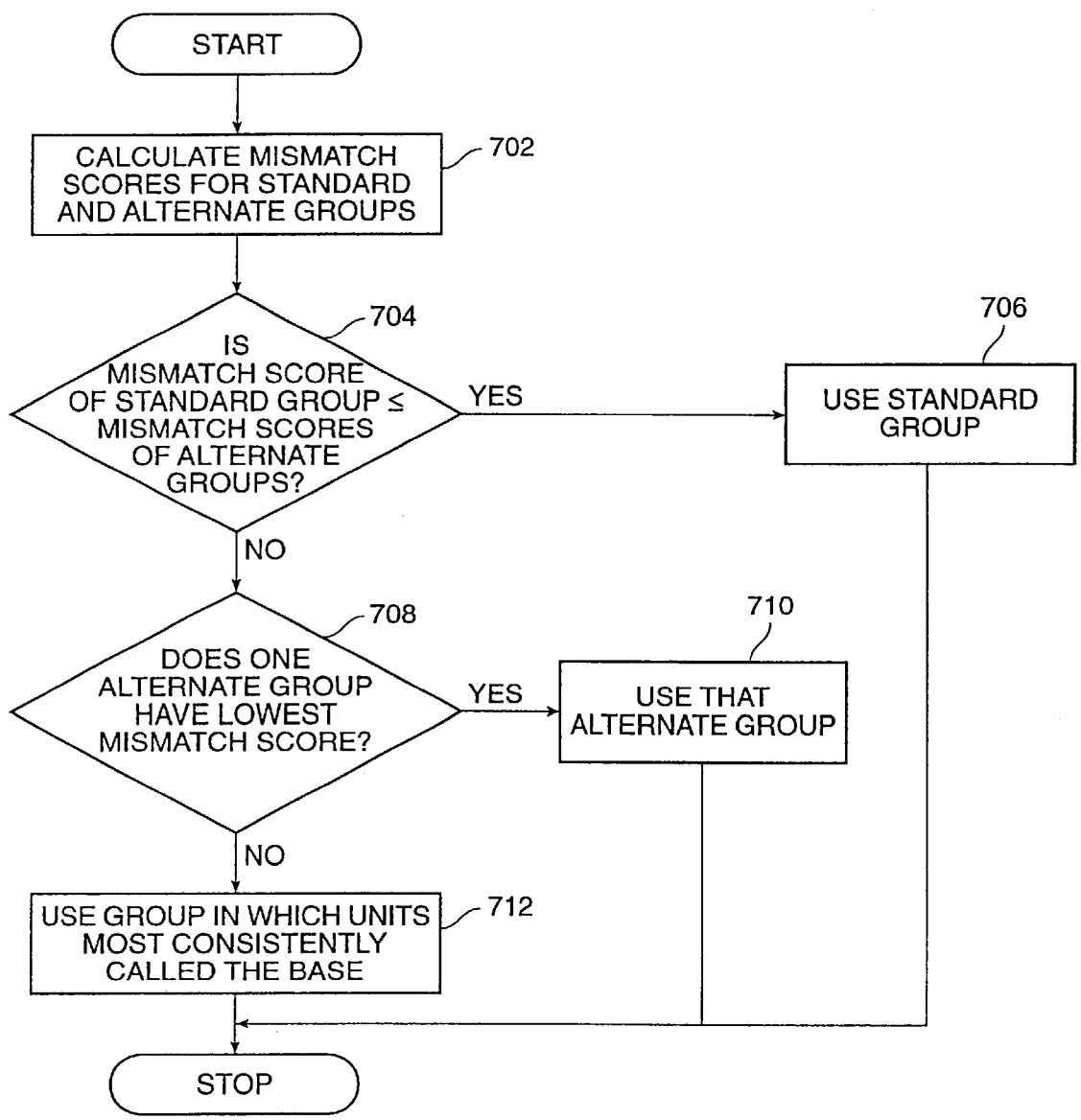
FIG. 16 is a flowchart of a process of selecting a best group of units for performing a base call.

FIG. 16 is a flowchart of a process of selecting a best group of units for performing a base call. Selecting the best group involves determining which reference sequence of the groups has the fewest mismatches with the target sequence near the interrogation position. The group of units that has the fewest mismatches near the interrogation position may have the highest likelihood of producing the most accurate base call. The window around the interrogation position which is analyzed may be a set value or set according to the probe structure. For example, if the maximum distance that the probes for all the groups extend from the interrogation position is eight base positions to one side of the interrogation position and ten base positions to the other side of the interrogation position, the window may be set as including this range of base positions.

At step 702, the system calculates mismatch scores for the standard and alternate groups of units. The mismatch score is an indication of how many mismatches a reference sequence appears to have with the target sequence. In order to determine a mismatch score, the system may only analyze base positions where at least two of the reference sequences differ. Thus, if all the reference sequences are identical at a base position, this base position may be skipped.

At each base position where at least two reference sequences differ, the system determines if the base call for a group (the base call indicating the likely base in the target sequence) at each of these positions differs from the corresponding base of the reference sequence. If the base call and the base for the reference sequence differ, the mismatch score is incremented by one. Initially, the mismatch scores for each group is set to zero.

Conceptually, it should be understood that the mismatch score is an indication of the number of base positions in a portion of the reference sequence that differ from the target sequence (optionally excluding those positions where all the reference sequences are the same). To better illustrate this concept, the following simple example is presented. Assume there is a standard group and two alternate groups as follows:

|  | Standard Group | | Mismatch Score |
|---|---|---|---|
| reference | ACGGAT<u>G</u>AGATACGA | (SEQ ID NO:3) | 1 |
| base calls | ACTGAT<u>G</u>AGATACGA | (SEQ ID NO:4) | |
|  | Alternate Group 1 | | Mismatch Score |
| reference | ACTGAT<u>G</u>AGATACGA | (SEQ ID NO:4) | 0 |
| base calls | ACTGAT<u>G</u>AGATACGA | (SEQ ID NO:4) | |
|  | Alternate Group 2 | | Mismatch Score |
| reference | ACGGAT<u>G</u>AGATACGT | (SEQ ID NO:5) | 2 |
| base calls | ACTGAT<u>G</u>AGATACGA | (SEQ ID NO:4) | |

The underlined bases correspond to the base position which is being analyzed. The bolded base positions indicate base positions where at least two of the reference sequences differ. At these bolded base positions, the standard group has one base position where the reference sequence differs from the target sequence (as indicated by the base calls) so the mismatch score is 1. Similarly, the first alternate group has a mismatch score of 0 and the second alternate group has a mismatch score of 2.

As alternate group 1 has the lowest mismatch score, that group would be utilized to call the base at the base position being analyzed. In this simple example, the base call is not different for any of the groups as this example is intended to illustrate how the best group may be selected. However, what is important is that the invention recognizes that the more mismatches that occur near a base position, the less accurate the base call will become. This result is brought upon by the fact that a mismatch between the reference sequence and the target sequence creates any area where the probes interrogating neighboring base positions include a single base mismatch. Single base mismatches lower the hybridization intensity and may produce inaccurate results.

At step 704, the system determines if a mismatch score of the standard groups is less than or equal to the mismatch scores of alternate groups. If the standard group has the lowest mismatch score (or ties), then the base call performed according to the standard group.

The system determines if a single alternate group has the lowest mismatch score at step 708. If so, that alternate group is utilized to make the base call at step 710. Otherwise, there are more than one alternate groups that have the same mismatch scores. If this is the case, the alternate group may be chosen which includes units that most consistently called the base at step 712. For example, if two alternate groups have the same lowest mismatch score but one group's units all called the same base and the other group's units were split, the alternate group that called the same base would be utilized. Other methods of determining the best group in the event of a mismatch score tie may also be utilized.

Figure 17A:
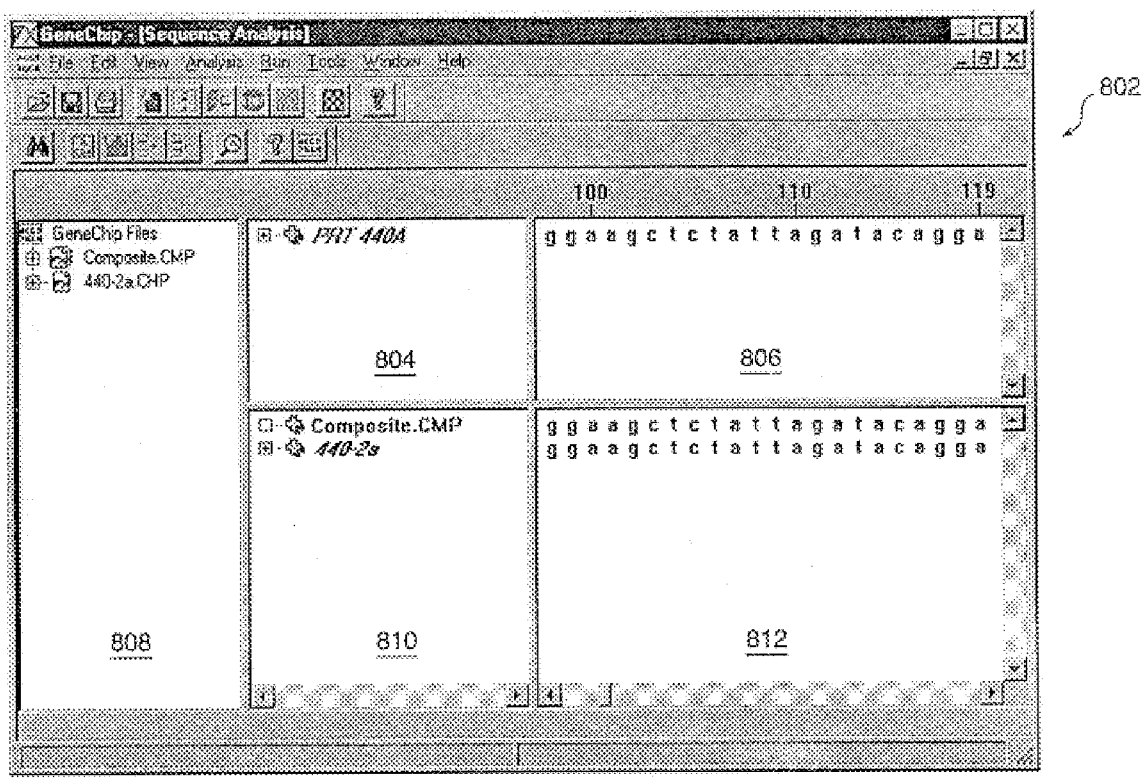
FIGS. 17A and 17B show screen displays allowing analysis of nucleotides from experiments from one or more chips (SEQ ID NO:2)

FIG. 17A shows a screen displays allowing analysis of nucleotides from experiments from one or more chips. A screen display 802 includes multiple screen areas that display different information to the user. A screen area 804 includes the name of a reference sequence which in this example is PRT 440A which are antisense regions (Protease Reverse Transcriptase) of the HIV virus. The reference sequence is typically used as a baseline with which to compare sample sequences. Although the reference sequence on the screen may be the chip wild-type sequence for which the chips were tiled, there is no requirement that this is the case.

A screen area 806 includes the nucleotide sequence for the reference sequence for the probe array. The base position of each nucleotide is shown above screen area 806. Screen area 806 also shows the reference sequence for each unit if "expanded" in the user interface.

A screen area 808 shows the user the chip and composite files that are currently being analyzed. A chip file (e.g., ends in ".CHP") includes data obtained from a single chip. A composite file (e.g., ends in ".CMP") includes data obtained from more than one chip. When a user opens a chip or composite file for analysis, the pathname of the file is displayed in screen area 808.

Information from the chip and composite files may be displayed in screen areas 810 and 812. Screen area 810 includes the names of sample sequences currently being analyzed from the chip or composite files. The name of the sample sequence is typically chosen to enable the user to readily determine the what the sample sequence represents. Screen area 812 includes the nucleotide sequence for the sample sequences. The base position of each nucleotide in screen area is the same as indicated above screen area 806. Accordingly, the system automatically aligns the reference and sample sequences for easier analysis.

Figure 17B:
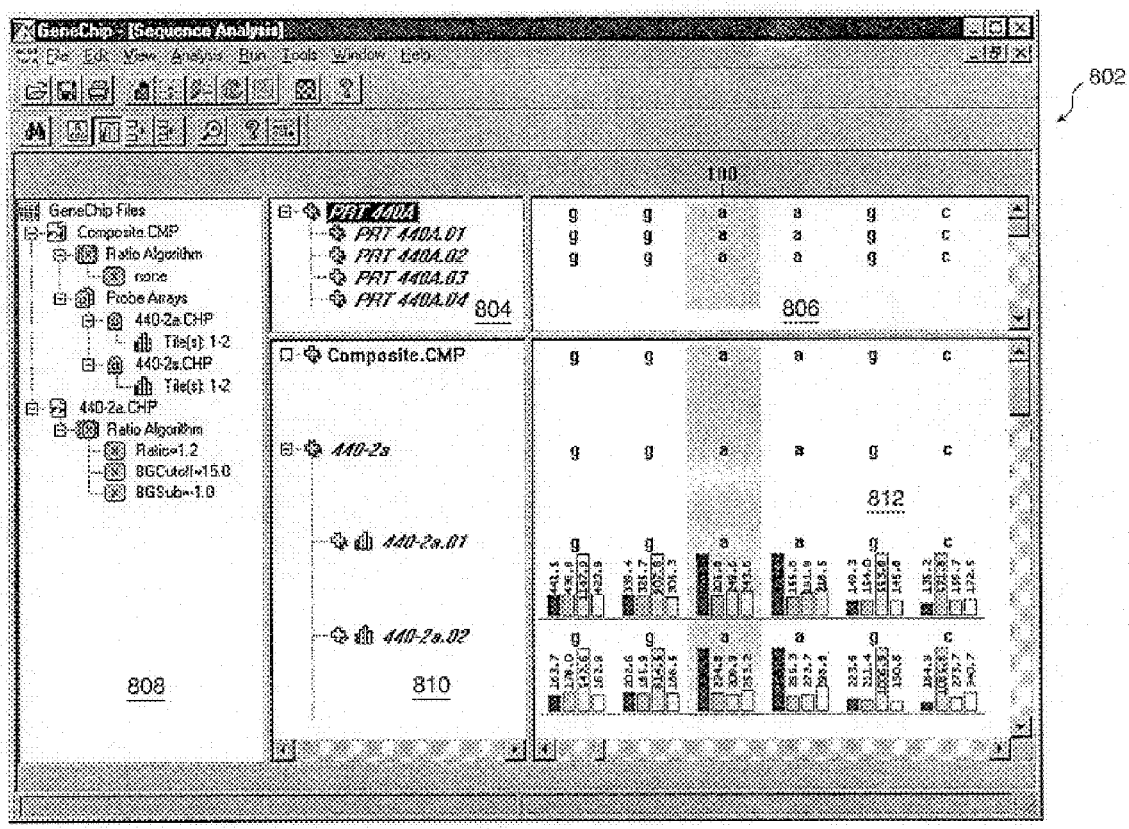

FIG. 17A has been described in order to familiarize the reader with the layout of the screen display. However, as illustrated by FIG. 17B, the invention allows the user to hide (not display) and summarize information from chip and composite files. For example, if a user "clicks on" or activates the screen icon plus sign in front of the composite filename in screen area 808, the system displays more information about the composite file. As shown, the method that was utilized to combine the information from the chip files may be shown along with the individual chip files.

Additionally, if a user activates the screen icon plus sign in front of the chip filename in screen area 808, the system displays more information about the chip file including the process or procedure that was utilized to calls bases. In FIG. 17B, the base calling procedure was the "Ratio Base Algorithm" which was described in reference to FIG. 10. Additionally, the user is able to modify parameters for the base calling procedure which will be immediately reflected in the base calls shown on the display screen. For example, the ratio cutoff ("Ratio") is displayed as 1.2. If a user increases the ratio cutoff to 1.4, the system would then recalculate the base calls for the chip and the new base calls would be reflected in screen area 812. The parameters may be any values the are input into the base calling procedure including constants, thresholds, ranges, and the like.

FIG. 17B also illustrates that the system is able to combine data from multiple experiments (including various tilings) for easier reading of the user. The sample sequence 440-2A was shown in FIG. 17A and has been expanded in FIG. 17B to show that the base calls are derived from multiple experiments, where the data from multiple experiments may be from a single chip or multiple chips. In other words, the nucleotide sequence shown for sample sequence 440-2A in FIGS. 17A and 17B do not represent a single experiment but actually a combination or consensus from multiple experiments. The user is able to review the data from each of the experiments as shown in FIG. 17B which includes displaying the hybridization intensities for each related base. The system allows the user to highlight a base position for analysis as shown for base position 100.

Referring again to FIG. 17A, a screen icon plus sign is displayed in front of the name of the sample sequence "440-2A." By activating the screen icon, the system displays each of the individual calls that make up the composite base call. As shown in FIG. 17B, the composite base call is derived from multiple base calls. The multiple base calls are aligned with the composite base call according to base position. The invention provides great flexibility to the user for displaying, hiding, and summarizing data for analyzing sequences.

Monitoring Gene Expression

Figure 18:
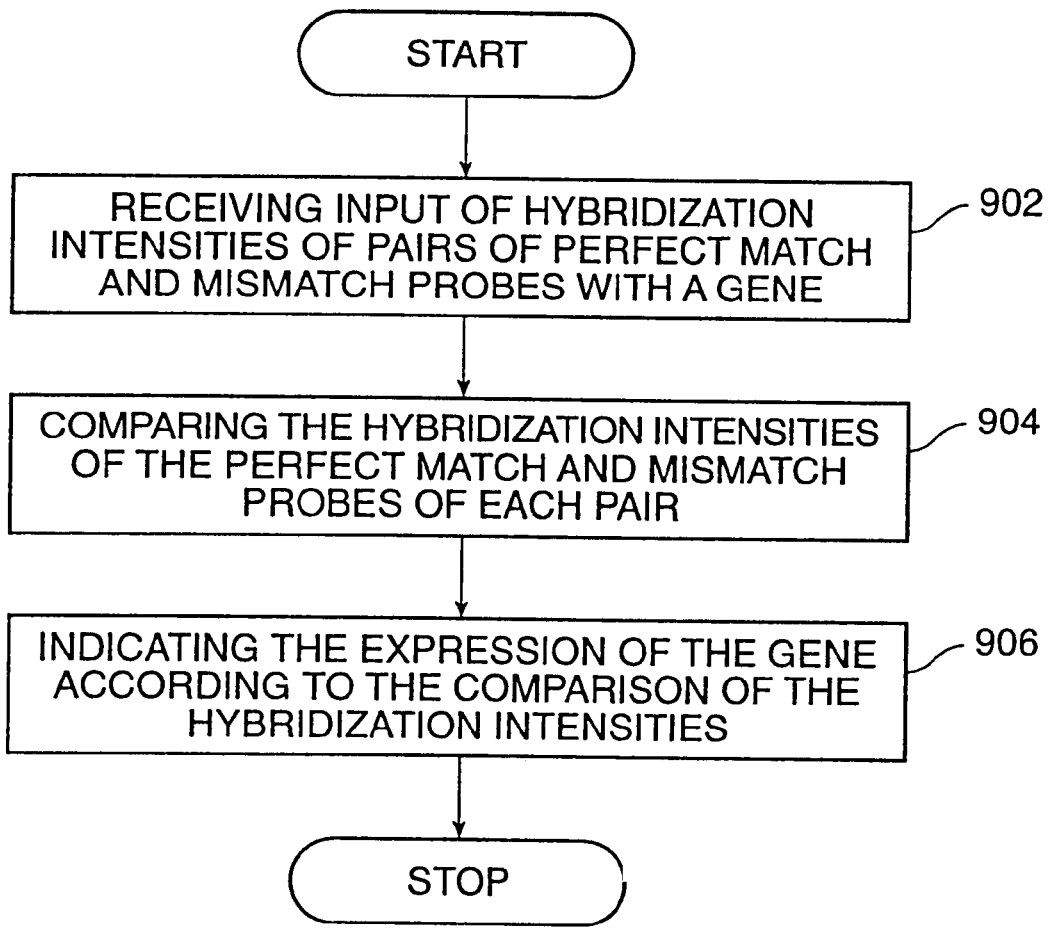
FIG. 18 shows a high level flowchart of a process of monitoring the expression of a gene by comparing hybridization intensities of pairs of perfect match and mismatch probes.

FIG. 18 shows a high level flowchart of a process of monitoring the expression of a gene by comparing hybridization intensities of pairs of perfect match and mismatch probes. The term "perfect match probe" refers to a probe that has a sequence that is perfectly complementary to a particular target sequence. The test probe is typically perfectly complementary to a portion (subsequence) of the target sequence. The term "mismatch control" or "mismatch probe" refer to probes whose sequence is deliberately selected not to be perfectly complementary to a particular target sequence. For each mismatch (MM) control in a high-density array there typically exists a corresponding perfect match (PM) probe that is perfectly complementary to the same particular target sequence.

The process compares hybridization intensities of pairs of perfect match and mismatch probes that are preferably covalently attached to the surface of a substrate or chip. Most preferably, the nucleic acid probes have a density greater than about 60 different nucleic acid probes per 1 cm$^2$ of the substrate. Although the flowcharts show a sequence of steps for clarity, this is not an indication that the steps must be performed in this specific order. One of ordinary skill in the art would readily recognize that many of the steps may be reordered, combined, and deleted without departing from the invention.

Initially, nucleic acid probes are selected that are complementary to the target sequence (or gene). These probes are the perfect match probes. Another set of probes is specified that are intended to be not perfectly complementary to the target sequence. These probes are the mismatch probes and each mismatch probe includes at least one nucleotide mismatch from a perfect match probe. Accordingly, a mismatch probe and the perfect match probe from which it was derived make up a pair of probes. As mentioned earlier, the nucleotide mismatch is preferably near the center of the mismatch probe.

The probe lengths of the perfect match probes are typically chosen to exhibit high hybridization affinity with the target sequence. For example, the nucleic acid probes may be all 20-mers. However, probes of varying lengths may also be synthesized on the substrate for any number of reasons including resolving ambiguities.

The target sequence is typically fragmented, labeled and exposed to a substrate including the nucleic acid probes as described earlier. The hybridization intensities of the nucleic acid probes is then measured and input into a computer system. The computer system may be the same system that directs the substrate hybridization or it may be a different system altogether. Of course, any computer system for use with the invention should have available other details of the experiment including possibly the gene name, gene sequence, probe sequences, probe locations on the substrate, and the like.

Referring to FIG. 18, after hybridization, the computer system receives input of hybridization intensities of the multiple pairs of perfect match and mismatch probes at step 902. The hybridization intensities indicate hybridization affinity between the nucleic acid probes and the target nucleic acid (which corresponds to a gene). Each pair includes a perfect match probe that is perfectly complementary to a portion of the target nucleic acid and a mismatch probe that differs from the perfect match probe by at least one nucleotide.

At step 904, the computer system compares the hybridization intensities of the perfect match and mismatch probes of each pair. If the gene is expressed, the hybridization intensity (or affinity) of a perfect match probe of a pair should be recognizably higher than the corresponding mismatch probe. Generally, if the hybridizations intensities of a pair of probes are substantially the same, it may indicate the gene is not expressed. However, the determination is not based on a single pair of probes, the determination of whether a gene is expressed is based on an analysis of many pairs of probes. An exemplary process of comparing the hybridization intensities of the pairs of probes will be described in more detail in reference to FIG. 19.

After the system compares the hybridization intensity of the perfect match and mismatch probes, the system indicates expression of the gene at step 906. As an example, the system may indicate an expression call to a user that the gene is either present (expressed), marginal or absent (unexpressed).

Figure 19:
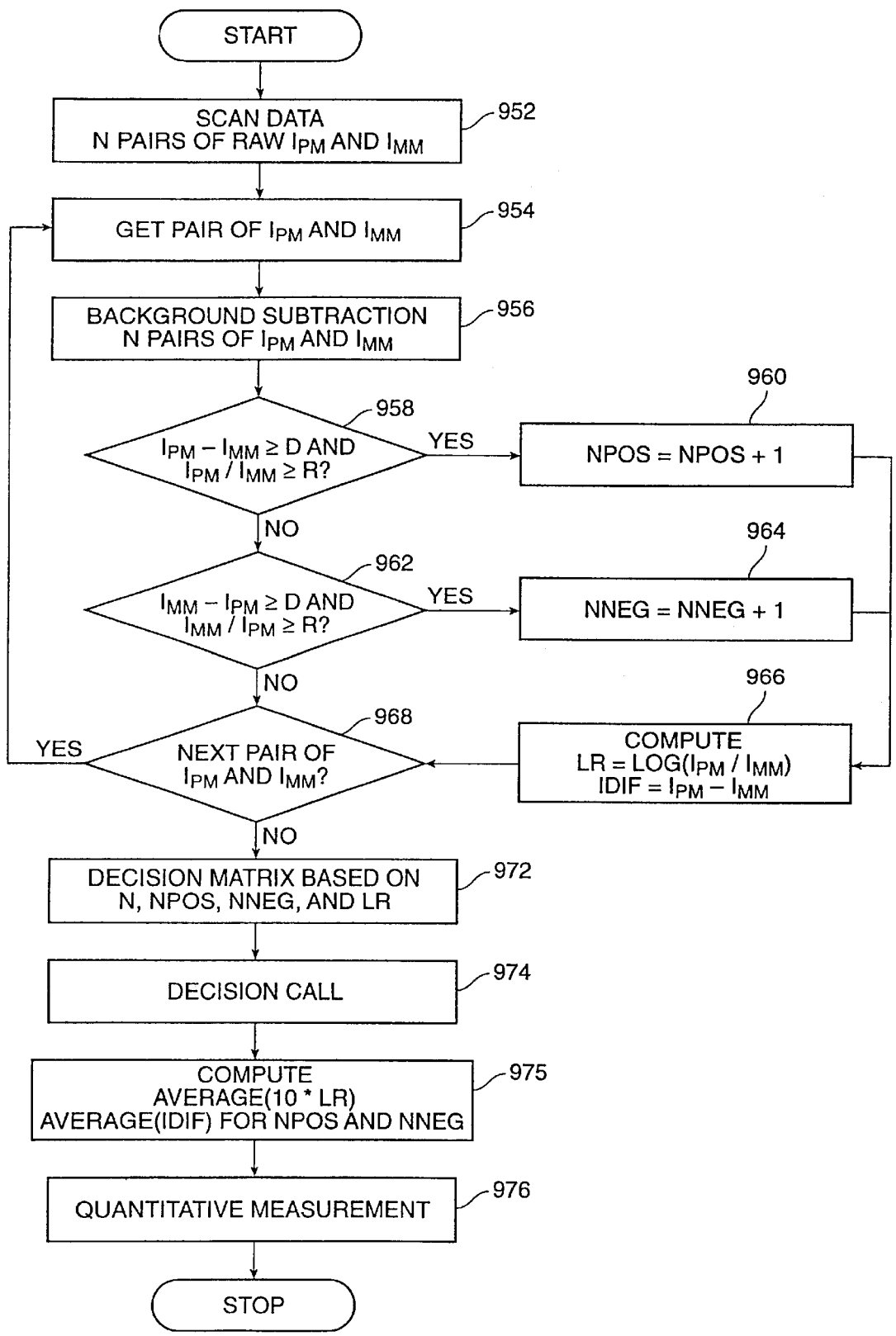
FIG. 19 shows a flowchart of a process of determining if a gene is expressed utilizing a decision matrix.

FIG. 19 shows a flowchart of a process of determining if a gene is expressed utilizing a decision matrix. At step 952, the computer system receives raw scan data of N pairs of perfect match and mismatch probes. In a preferred embodiment, the hybridization intensities are photon counts from a fluorescein labeled target that has hybridized to the probes on the substrate. For simplicity, the hybridization intensity of a perfect match probe will be designed "$I_{pm}$" and the hybridization intensity of a mismatch probe will be designed "$I_{mm}$."

Hybridization intensities for a pair of probes is retrieved at step 954. The background signal intensity is subtracted from each of the hybridization intensities of the pair at step 956. Background subtraction may also be performed on all the raw scan data at the same time.

At step 958, the hybridization intensities of the pair of probes are compared to a difference threshold (D) and a ratio threshold (R). It is determined if the difference between the hybridization intensities of the pair ($I_{pm}-I_{mm}$) is greater than or equal to the difference threshold AND the quotient of the hybridization intensities of the pair ($I_{pm}/I_{mm}$) is greater than or equal to the ratio threshold. The difference thresholds are typically user defined values that have been determined to produce accurate expression monitoring of a gene or genes. In one embodiment, the difference threshold is 20 and the ratio threshold is 1.2.

If $I_{pm}-I_{mm}>=D$ and, $I_{pm}/I_{mm}>=R$, the value NPOS is incremented at step 960. In general, NPOS is a value that indicates the number of pairs of probes which have hybridization intensities indicating that the gene is likely expressed. NPOS is utilized in a determination of the expression of the gene.

At step 962, it is determined if $I_{mm}-I_{pm}>=D$ and $I_{mm}/I_{pm}>=R$. If this expression is true, the value NNEG is incremented at step 964. In general, NNEG is a value that indicates the number of pairs of probes which have hybridization intensities indicating that the gene is likely not expressed. NNEG, like NPOS, is utilized in a determination of the expression of the gene.

For each pair that exhibits hybridization intensities either indicating the gene is expressed or not expressed, a log ratio value (LR) and intensity difference value (IDIF) are calculated at step 966. LR is calculated by the log of the quotient of the hybridization intensities of the pair $(I_{pm}/I_{mm})$. The IDIF is calculated by the difference between the hybridization intensities of the pair $(I_{pm}-I_{mm})$. If there is a next pair of hybridization intensities at step 968, they are retrieved at step 954.

At step 972, a decision matrix is utilized to indicate if the gene is expressed. The decision matrix utilizes the values N, NPOS, NNEG, and LR (multiple LRs). The following four assignments are performed:

P1=NPOS/NNEG

P2=NPOS/N

P3=(10 * SUM(LR))/(NPOS+NNEG)

These P values are then utilized to determine if the gene is expressed.

For purposes of illustration, the P values are broken down into ranges. If P1 is greater than or equal to 2.1, then A is true. If P1 is less than 2.1 and greater than or equal to 1.8, then B is true. Otherwise, C is true. Thus, P1 is broken down into three ranges A, B and C. This is done to aid the readers understanding of the invention.

Thus, all of the P values are broken down into ranges according to the following:

A=(P1>=2.1)

B=(2.1>P1>=1.8)

C=(P1<1.8)

X=(P2>=0.35)

Y=(0.35>P2>=0.20)

Z=(P2<0.20)

Q=(P3>=1.5)

R=(1.5>P3>=1.1)

S=(P3<1.1)

Once the P values are broken down into ranges according to the above boolean values, the gene expression is determined.

The gene expression is indicated as present (expressed), marginal or absent (not expressed). The gene is indicated as expressed if the following expression is true: A and (X or Y) and (Q or R). In other words, the gene is indicated as expressed if P1>=2.1, P2>=0.20 and P3>=1.1. Additionally, the gene is indicated as expressed if the following expression is true: B and X and Q.

With the forgoing explanation, the following is a summary of the gene expression indications:

| | |
|---|---|
| Present | A and (X or Y) and (Q or R) |
| | B and X and I |
| Marginal | A and X and S |
| | B and X and R |
| | B and Y and (Q or R) |
| Absent | All others cases (e.g., any C combination) |

In the output to the user, present may be indicated as "P," marginal as "M" and absent as "A" at step 974.

Once all the pairs of probes have been processed and the expression of the gene indicated, an average of ten times the LRs is computed at step 975. Additionally, an average of the IDIF values for the probes that incremented NPOS and NNEG is calculated, which may be utilized as an expression level. These values may be utilized for quantitative comparisons of this experiments with other experiments.

Quantitative measurements may be performed at step 976. For example, the current experiment may be compared to a previous experiment (e.g., utilizing values calculated at step 970). Additionally, the experiment may be compared to hybridization intensities of RNA (such as from bacteria) present in the biological sample in a known quantity. In this manner, one may verify the correctness of the gene expression indication or call, modify threshold values, or perform any number of modifications of the preceding.

For simplicity, FIG. 19 was described in reference to a single gene. However, the process may be utilized on multiple genes in a biological sample. Therefore, any discussion of the analysis of a single gene is not an indication that the process may not be extended to processing multiple genes.

Figure 20:
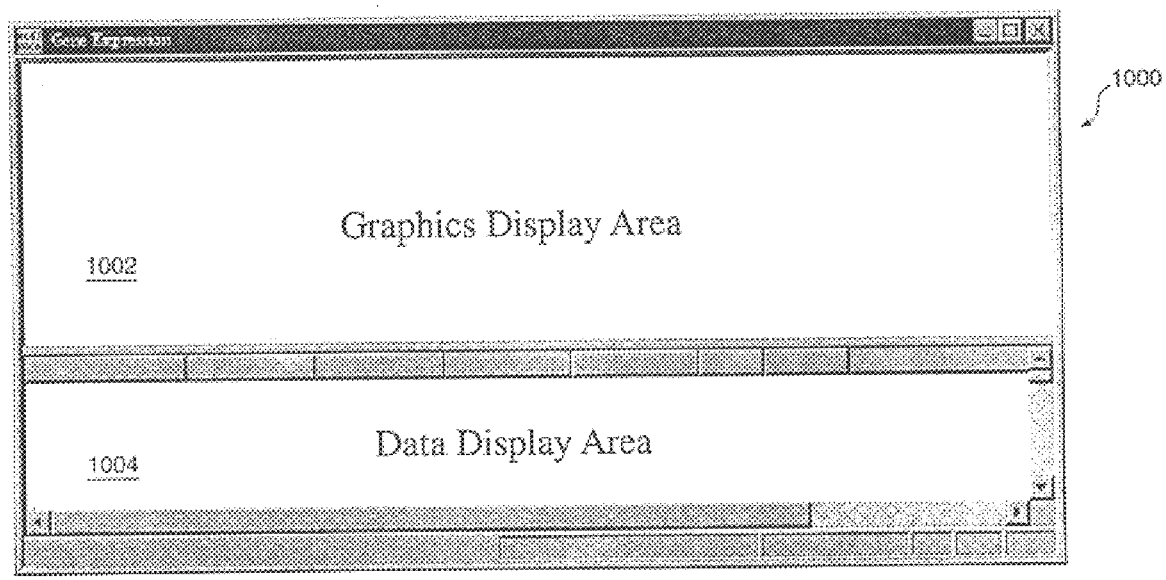
FIG. 20 shows a screen display layout of gene expression monitoring software.

FIG. 20 shows a screen display layout of gene expression monitoring software. A screen display 1000 is divided into two sections: a graphics display area 1002 and a data display area 1004. The graphics display area is for displaying graphs which will aid the user in interpreting the data. The data display area is for displaying the underlying data so the user may evaluate the underlying data for gene expression.

As will be shown in subsequent screen displays, the data display area is preferably organized in a table having rows and columns. Each column has a heading indicating the data that resides in the column. Each row represents data from a single experiment or combination of experiments for a gene. The term "experiment" is used herein to describe a process that created data. For example, a single image file of a hybridized chip may produce many "experiments" for a number of genes. Additionally, experiments may refer to data obtained from different chips.

Figure 21A:
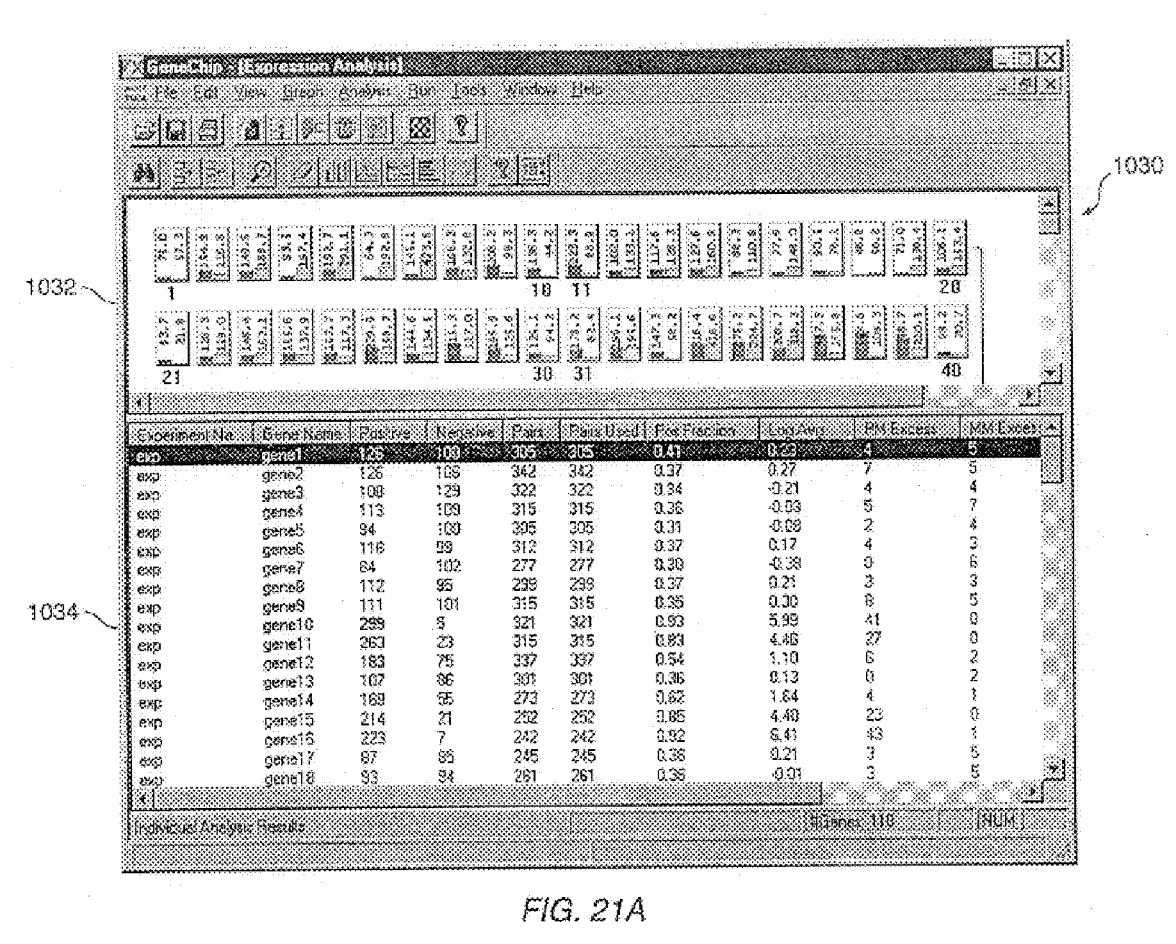

FIG. 21A shows a screen display illustrating the analysis of a selected gene. A screen display 1030 includes a graphics display area that illustrates with bar graphs the hybridization intensities of perfect match probes and mismatch probes at each base position in a selected gene. The gene selected is shown highlighted in a data display area 1034.

The data display area includes a number of column headings. The Experiment Name refers to a user-defined name for the experiment. The Gene Name is the name of the gene. The numbers Positive and Negative refer to the values NPOS and NNEG as described in reference to FIG. 19. The Pairs column indicates the number of perfect match and mismatch probe pairs that were utilized in the analysis of the gene. The Pos Fraction column indicates the fraction of probe pairs that were scored as positive (i.e., Positive/Pairs).

Figure 21B:
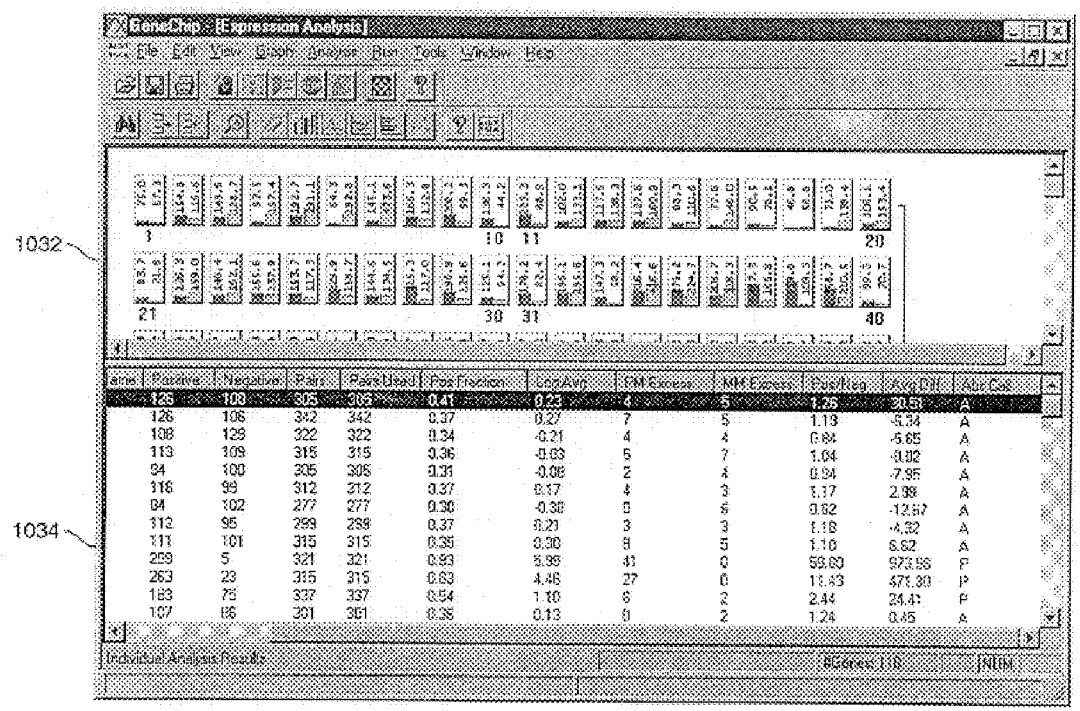

The Avg Ratio column indicates the average of $I_{pm}/I_{mm}$ for all probes for a gene. The Log Avg column indicates the average of the $\log(I_{pm}/I_{mm})$. The PM Excess column indicates the number of perfect match probes that exhibit a hybridization intensity above a user defined threshold. The MM Excess indicates the number of mismatch probes that exhibit a hybridization intensity above a user defined threshold. Referring now to FIG. 21B, the Pos/Neg column indicates ratio of the Positive column to the Negative column ("Inf" is utilized if the Negative column includes a zero). The Avg Diff column indicates the average intensity difference for the gene. The average intensity difference was computed at step 975 of FIG. 19 (i.e., average(IDIF)).

The Abs Call column indicates the gene expression call for the experiment. The values in this column may be "P" for present, "M" for marginal and "A" for absent. The gene expression call for a preferred embodiment is described in more detail in reference to step 974 of FIG. 19.

As the user selects an experiment, the graphics display area displays graphs to aid the user in interpreting the data. A button bar 1034 enables the user to select which graph or graphs to display in the graphics display area. Additionally, the user is able to sort the data in the display data are according to values in a selected column.

Figure 22:
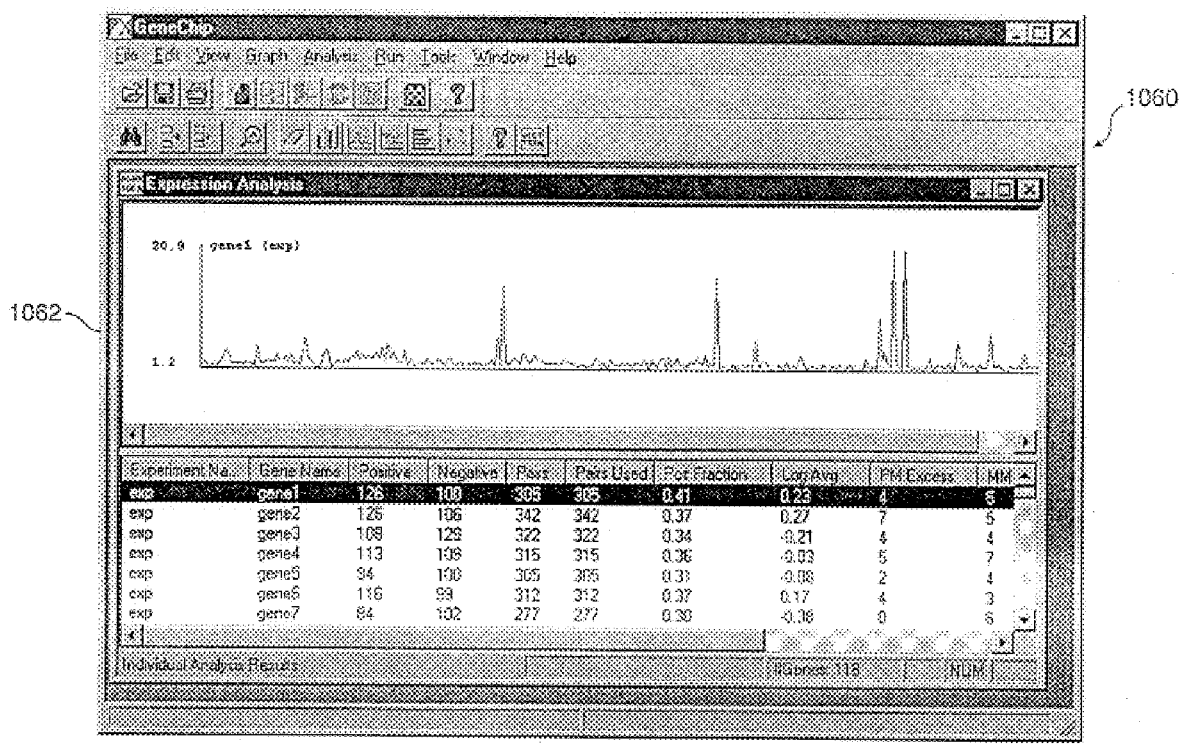
FIG. 22 shows another screen display illustrating the analysis of a selected gene.

FIG. 22 shows another screen display illustrating the analysis of a selected gene. A screen display 1060 includes a graphics display area 1062 illustrating a graph of the ratio of the hybridization intensity of the perfect match probe to the mismatch probe at each base position. The x-axis is the base position and the y-axis is the ratio of hybridization intensities. The statistical ratio threshold is plotted on the graph, which in this example is 1.2. this graph may be utilized by the user to analyze how many probe pairs ($I_{pm}/I_{mm}$) are above or below the threshold. The graph also includes the gene and experiment names.

Figure 23:
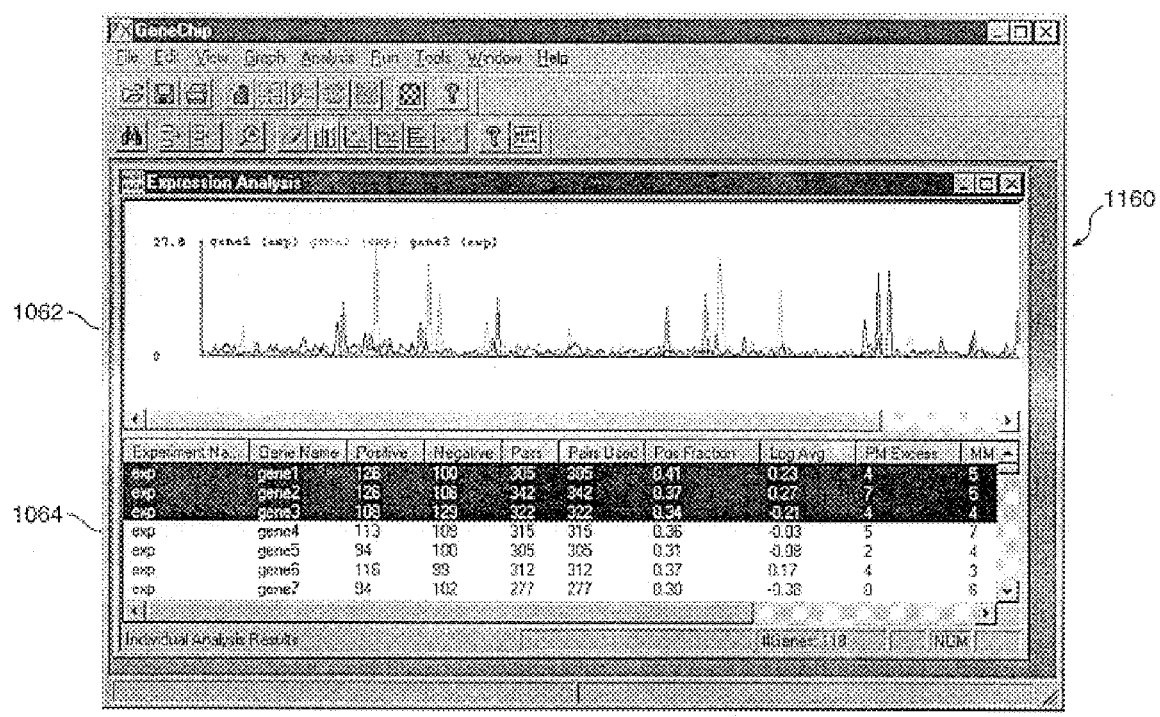
FIG. 23 shows a screen display illustrating the comparison of experiments for selected genes.

FIG. 23 shows a screen display illustrating the comparison of experiments for selected genes. A screen display 1160 includes a graphics display area 1062 and a data display are 1164. The graphics display area includes a graph of the ratio of the hybridization intensity of the perfect match probe to the mismatch probe at each base position for each of the experiments/genes selected in the data display area. In a preferred embodiment, the experiment name, gene name, and data plot are a different color for each gene to allow the user to more easily see the differences between or among selected genes.

Figure 24:
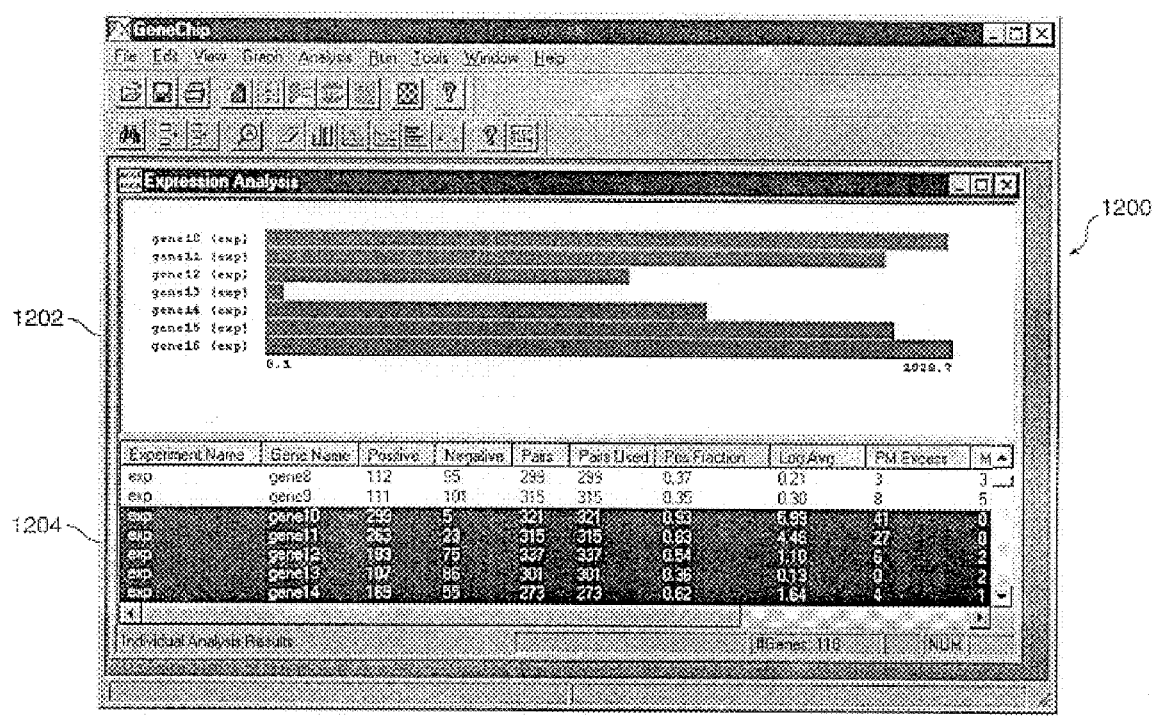
FIG. 24 shows another screen display illustrating the comparison of experiments for selected genes.

FIG. 24 shows another screen display illustrating the comparison of experiments for selected genes. A screen display 1200 includes a graphics display area 1202 illustrating the expression levels of genes selected in a data display area 1204. The graph of the expression levels of the selected genes is a bar graph. In a preferred embodiment, the expression level is defined as the average intensity difference (see average(IDIF) in FIG. 19). The graph also includes the gene and experiment names.

Figure 25:
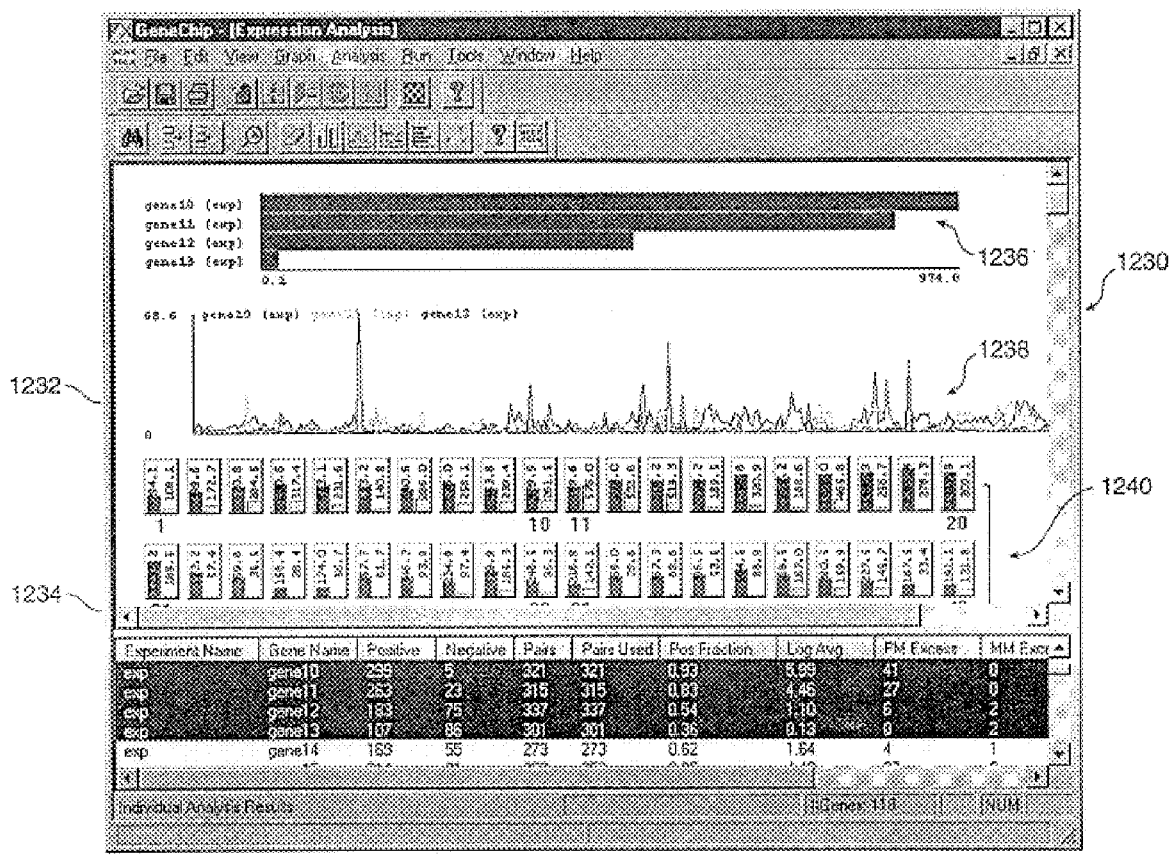
FIG. 25 shows another screen display illustrating the comparison of experiments for selected genes with multiple graphs in the graphics display area.

FIG. 25 shows another screen display illustrating the comparison of experiments for selected genes with multiple graphs in the graphics display area. A screen display 1230 includes a graphics display area 1232 depicting multiple graphs for analyzing the genes selected in a data display area 1234. An expression level graph 1236, an average intensity difference graph 1238 and a hybridization intensity graph 1240 are shown for the selected genes.

Figure 26A:
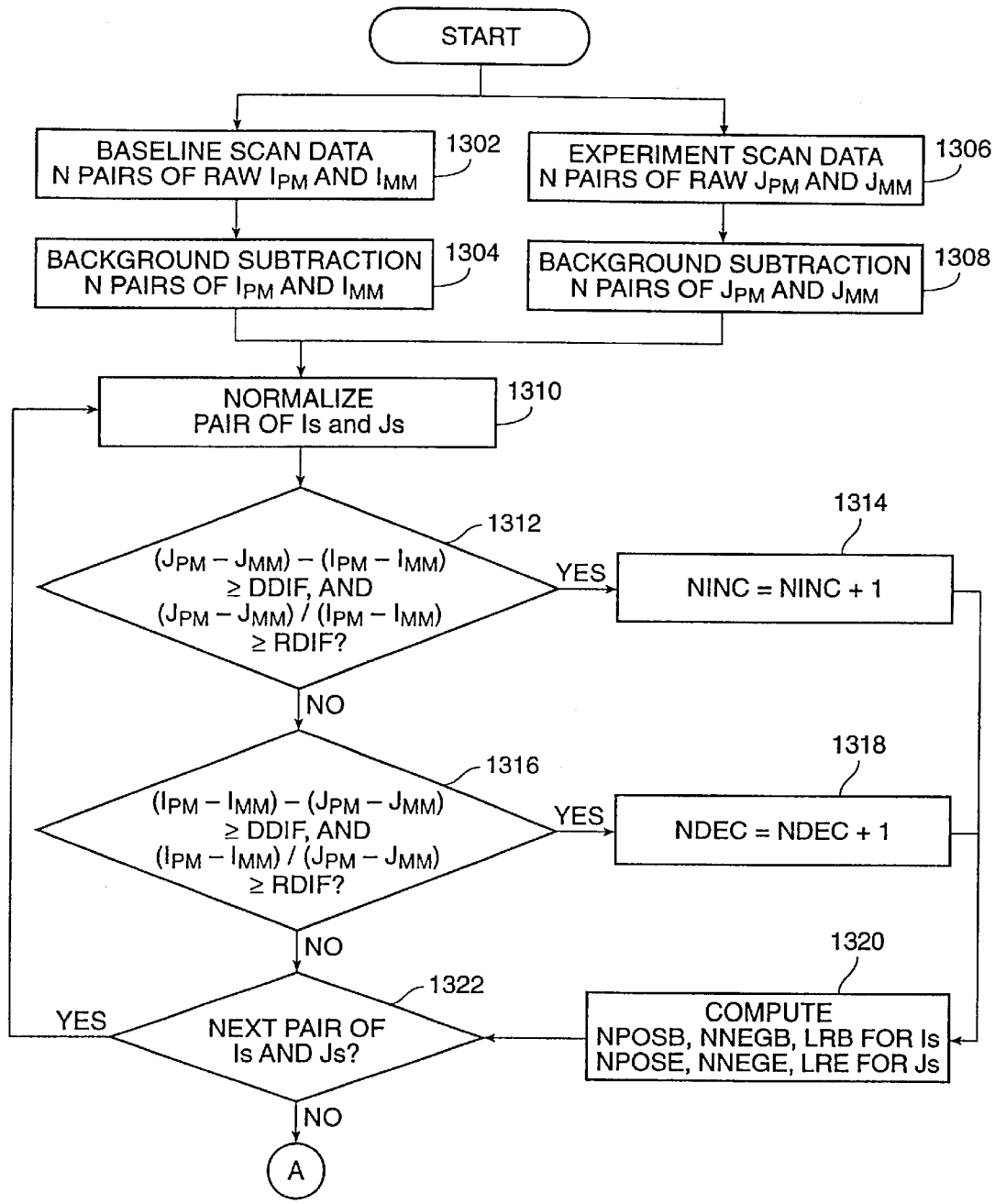
FIGS. 26A and 26B show a flowchart of a process of determining the expression of a gene by comparing baseline scan data and experimental scan data.
Figure 26B:
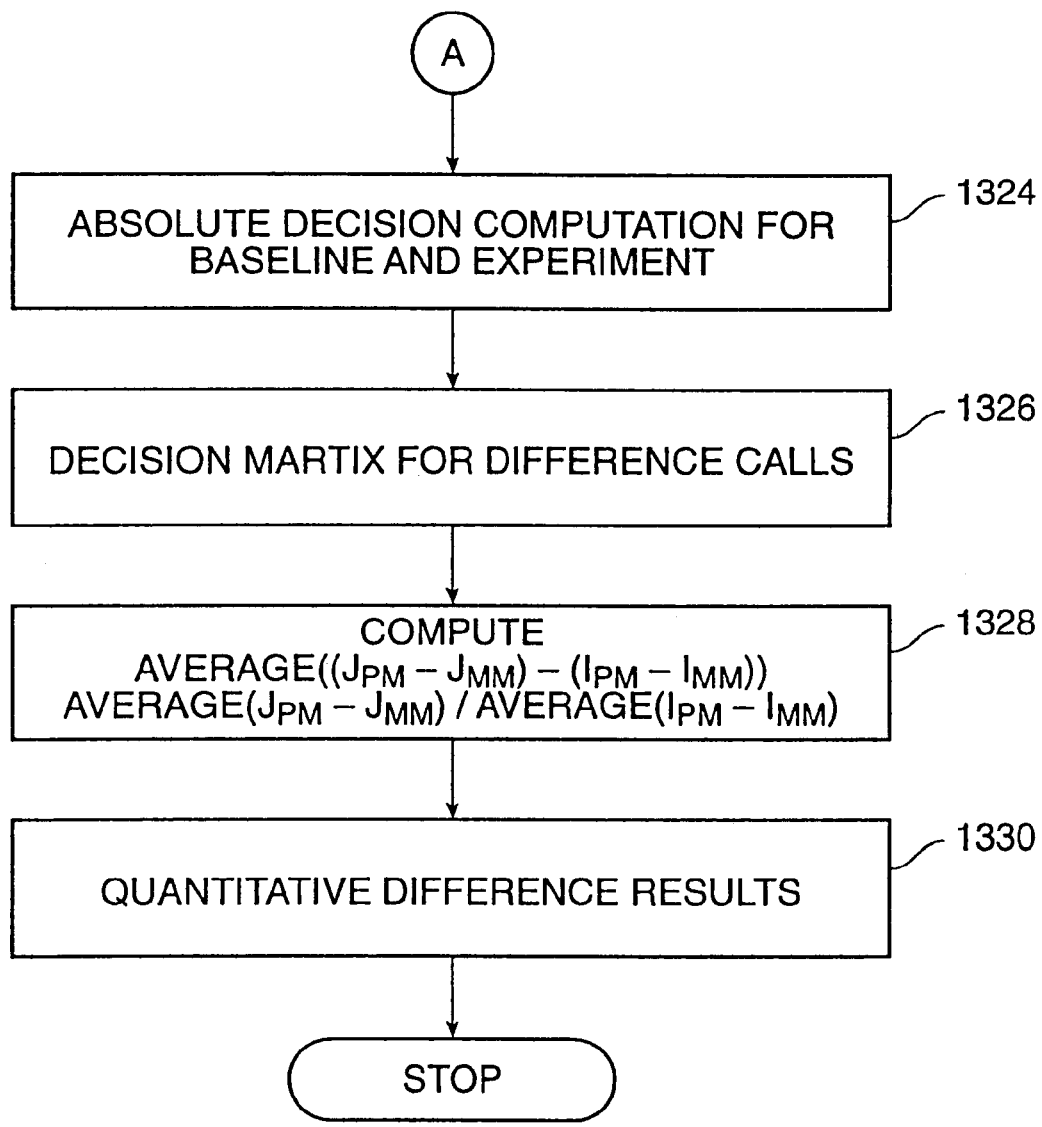

FIGS. 26A and 26B show the flow of a process of determining the expression of a gene by comparing baseline scan data and experimental scan data. For example, the baseline scan data may be from a biological sample where it is known the gene is expressed. Thus, this scan data may be compared to a different biological sample to determine if the gene is expressed. Additionally, it may be determined how the expression of a gene or genes changes over time in a biological organism. Accordingly, the term "baseline" means that it will be used as a point of reference.

At step 1302, the computer system receives raw scan data of N pairs of perfect match and mismatch probes from the baseline. The hybridization intensity of a perfect match probe from the baseline will be designed "$I_{pm}$" and the hybridization intensity of a mismatch probe from the baseline will be designed "$I_{mm}$." The background signal intensity is subtracted from each of the hybridization intensities of the pairs of baseline scan data at step 1304.

At step 1306, the computer system receives raw scan data of N pairs of perfect match and mismatch probes from the experimental biological sample. The hybridization intensity of a perfect match probes from the experiment will be designed "$J_{pm}$" and the hybridization intensity of a mismatch probe from the experiment will be designed "$J_{mm}$." The background signal intensity is subtracted from each of the hybridization intensities of the pairs of experimental scan data at step 1308.

The hybridization intensities of an I and J pair may be normalized at step 1310. For example, the hybridization intensities of the I and J pairs may be divided by the hybridization intensity of control probes.

At step 1312, the hybridization intensities of the I and J pair of probes are compared to a difference threshold (DDIF) and a ratio threshold (RDIF). It is determined if the difference between the hybridization intensities of the one pair ($J_{pm}-J_{mm}$) and the other pair ($I_{pm}-I_{mm}$) are greater than or equal to the difference threshold AND the quotient of the hybridization intensities of one pair ($J_{pm}-J_{mm}$) and the other pair ($I_{pm}-I_{mm}$) are greater than or equal to the ratio threshold. The difference thresholds are typically user defined values that have been determined to produce accurate expression monitoring of a gene or genes.

If ($J_{pm}-J_{mm}$)−($I_{pm}-I_{mm}$)>=DDIF and ($J_{pm}-J_{mm}$)/($I_{pm}-I_{mm}$) >=RDIF, the value NINC is incremented at step 1314. In general, NINC is a value that indicates the experimental pair of probes indicates that the gene expression is likely greater (or increased) than the baseline sample. NINC is utilized in a determination of whether the expression of the gene is greater (or increased), less (or decreased) or did not change in the experimental sample compared to the baseline sample.

At step 1316, it is determined if ($J_{pm}-J_{mm}$)−($I_{pm}-I_{mm}$)>= DDIF and ($J_{pm}-J_{mm}$)/($I_{pm}-I_{mm}$)>=RDIF. If this expression is true, NDEC is incremented. In general, NDEC is a value that indicates the experimental pair of probes indicates that the gene expression is likely less (or decreased) than the baseline sample. NDEC is utilized in a determination of whether the expression of the gene is greater (or increased), less (or decreased) or did not change in the experimental sample compared to the baseline sample.

For each of the pairs that exhibits hybridization intensities either indicating the gene is expressed more or less in the experimental sample, the values NPOS, NNEG and LR are calculated for each pair of probes. These values are calculated as discussed above in reference to FIG. 19. A suffix of either "B" or "E" has been added to each value in order to indicate if the value denotes the baseline sample or the experimental sample, respectively. If there are next pairs of hybridization intensities at step 1322, they are processed in a similar manner as shown.

Referring now to FIG. 26B, an absolute decision computation is performed for both the baseline and experimental samples at step 1324. The absolute decision computation is an indication of whether the gene is expressed, marginal or absent in each of the baseline and experimental samples. Accordingly, in a preferred embodiment, this step entails performing steps 972 and 974 from FIG. 19 for each of the samples. This being done, there is an indication of gene expression for each of the samples taken alone.

At step 1326, a decision matrix is utilized to determine the difference in gene expression between the two samples. This decision matrix utilizes the values, N, NPOSB, NPOSE, NNEGB, NNEGE, NINC, NDEC, LRB, and LRE as they were calculated above. The decision matrix performs different calculations depending on whether NINC is greater than or equal to NDEC. The calculations are as follows.

If NINC>=NDEC, the following four P values are determined:

P1=NINC/NDEC

P2=NINC/N

P3=((NPOSE−NPOSB)−(NNEGE−NNEGB))/N

P4=10*SUM(LRE−LRB)/N

These P values are then utilized to determine the difference in gene expression between the two samples.

For purposes of illustration, the P values are broken down into ranges as was done previously. Thus, all of the P values are broken down into ranges according to the following:

A=(P1>=2.8)

B=(2.8>P1>=2.0)

C=(P1<2.0)

X=(P2>=0.34)

Y=(0.34>P2>=0.24)

Z=(P2<0.24)

M=(P3>=0.20)

N=(0.20>P3>=0.12)

O=(P3<0.12)

Q=(P4>=0.9)

R=(0.9>P4>=0.5)

S=(P4<0.5)

Once the P values are broken down into ranges according to the above boolean values, the difference in gene expression between the two samples is determined.

In this case where NINC>=NDEC, the gene expression change is indicated as increased, marginal increase or no change. The following is a summary of the gene expression indications:

| | |
|---|---|
| Increased | A and (X or Y) and (Q or R) and (M or N or O) |
| | A and (X or Y) and (Q or R or S) and (M or N) |
| | B and (X or Y) and (Q or R) and (M or N) |
| | A and X and (Q or R or S) and (M or N or O) |
| Marginal | A or Y or S or O |
| Increase | B and (X or Y) and (Q or R) and O |
| | B and (X or Y) and S and (M or N) |
| | C and (X or Y) and (Q or R) and (M or N) |
| No Change | All others cases (e.g., any Z combination) |

In the output to the user, increased may be indicated as "I," marginal increase as "MI" and no change as "NC."

If NINC<NDEC, the following four P values are determined:

P1=NDEC/NINC

P2=NDEC/N

P3=((NNEGE−NNEGB)−(NPOSE−NPOSB))/N

P4=10 * SUM(LRE−LRB)/N

These P values are then utilized to determine the difference in gene expression between the two samples.

The P values are broken down into the same ranges as for the other case where NINC>=NDEC. Thus, P values in this case indicate the same ranges and will not be repeated for the sake of brevity. However, the ranges generally indicate different changes in the gene expression between the two samples as shown below.

In this case where NINC<NDEC, the gene expression change is indicated as decreased, marginal decrease or no change. The following is a summary of the gene expression indications:

| | |
|---|---|
| Decreased | A and (X or Y) and (Q or R) and (M or N or O) |
| | A and (X or Y) and (Q or R or S) and (M or N) |
| | B and (X or Y) and (Q or R) and (M or N) |
| | A and X and (Q or R or S) and (M or N or O) |
| Marginal | A or Y or S or O |
| Decrease | B and (X or Y) and (Q or R) and O |
| | B and (X or Y) and S and (M or N) |
| | C and (X or Y) and (Q or R) and (M or N) |
| No Change | All others cases (e.g., any Z combination) |

In the output to the user, decreased may be indicated as "D," marginal decrease as "MD" and no change as "NC."

The above has shown that the relative difference between the gene expression between a baseline sample and an experimental sample may be determined. An additional test may be performed that would change an I, MI, D, or MD (i.e., not NC) call to NC if the gene is indicated as expressed in both samples (e.g., from step 1324) and the following expressions are all true:

Average(IDIFB)>=200

Average(IDIFE)>=200

1.4>=Average(IDIFE)/Average(IDIFB)>=0.7

Thus, when a gene is expressed in both samples, a call of increased or decreased (whether marginal or not) will be changed to a no change call if the average intensity difference for each sample is relatively large or substantially the same for both samples. The IDIFB and IDIFE are calculated as the sum of all the IDIFs for each sample divided by N.

At step 1328, values for quantitative difference evaluation are calculated. An average of $((J_{pm}-J_{mm})-(I_{pm}-I_{mm}))$ for each of the pairs is calculated. Additionally, a quotient of the average of $J_{pm}-J_{mm}$ and the average of $I_{pm}-I_{mm}$ is calculated. These values may be utilized to compare the results with other experiments in step 1330.

Figure 27A:
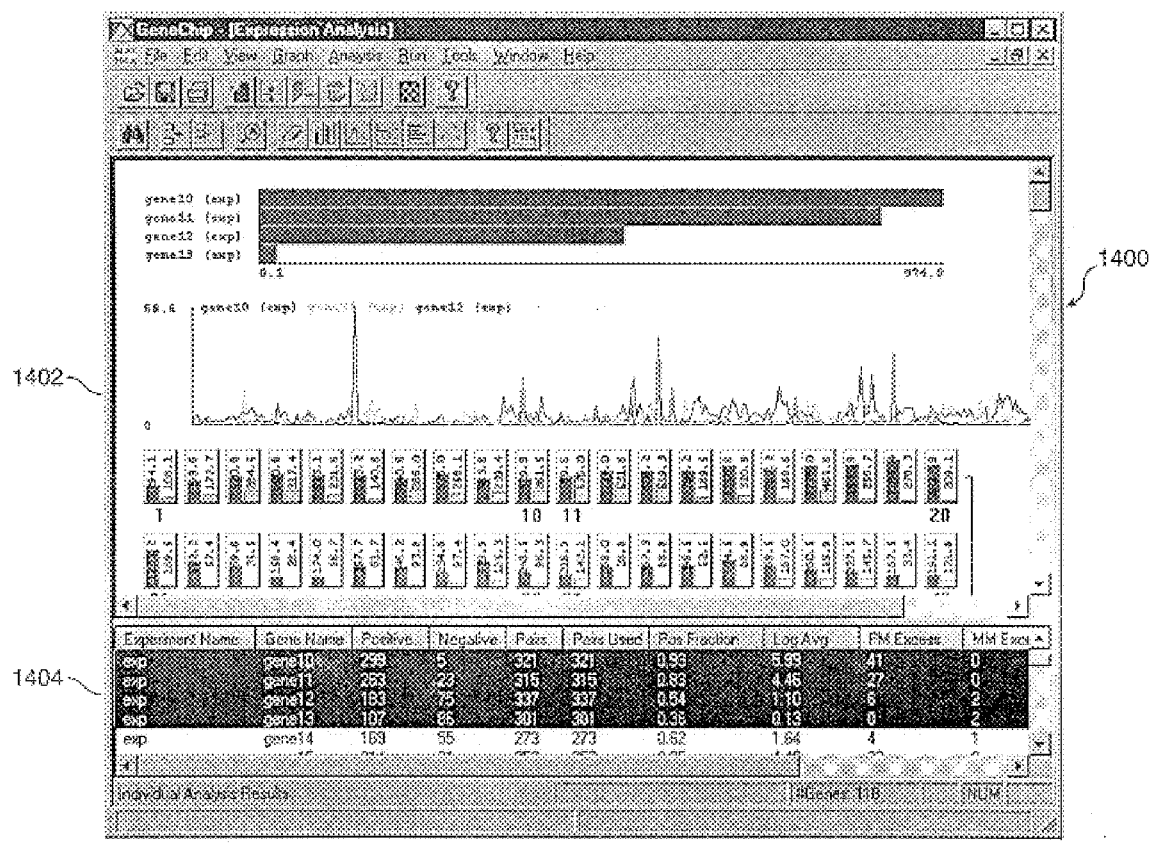
Figure 27B:
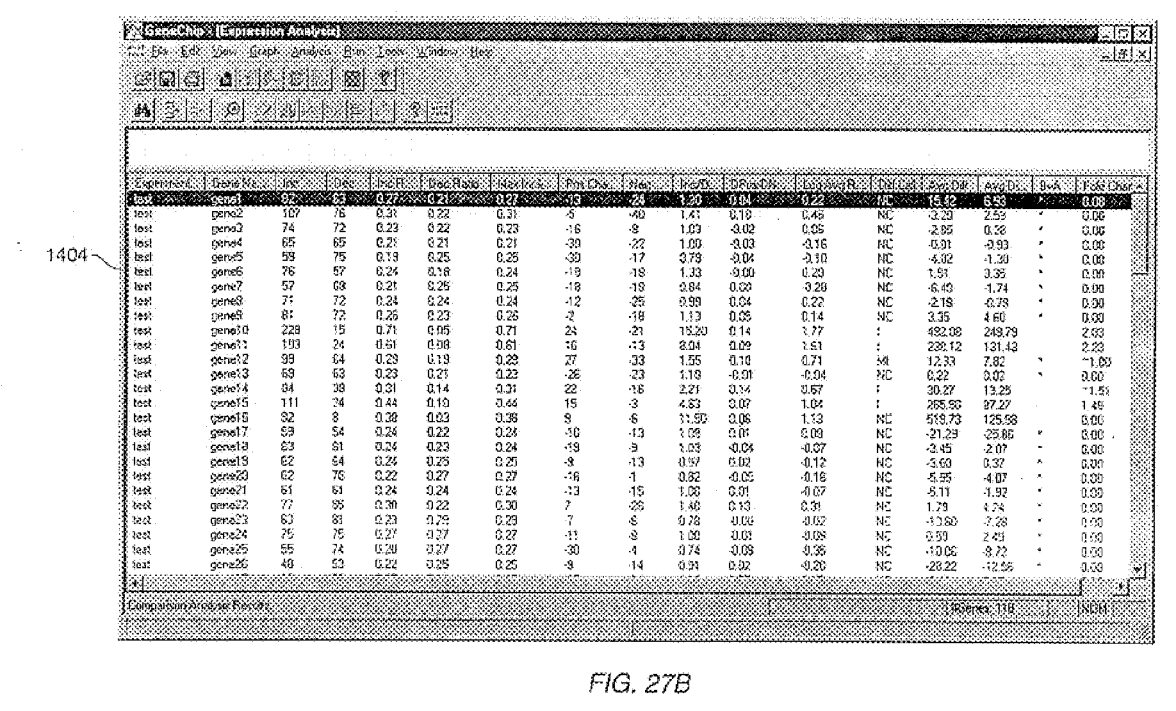

FIG. 27A shows a screen display illustrating the monitoring of the change of gene expression between experiments. A screen display 1400 includes a graphics display area 1402 and a data display area 1404. A user begins the comparison of experiments for a gene by selecting two experiments for a gene. For simplicity, we will call one baseline data and the other experimental data, meaning it will be compared to the baseline. For example, a user may select two experiments for the gene with the name "g182506." A comparison of two experiments is an experiment itself so the user is able to enter an experiment name which was entered as "foo" in the data display area of FIG. 27A. FIG. 27B shows another screen display illustrating monitoring of the change of gene expression between experiments.

The system then determines the change in gene expression between the selected experiments according to the process described in FIGS. 28A and 28B. The data display area includes columns denoting the data produced by this comparison. The Experiment Name refers to a user-defined name for the comparison experiment. The Gene Name is the name of the gene. The numbers Inc and Dec refer to the values NINC and NDEC as described in reference to FIG. 26A. More specifically, Inc refers to the number of base positions in the gene for which the difference and ratio of the perfect match and mismatch hybridization intensities are significantly greater in the experimental data.

The Inc Ratio column indicates the number of base positions where the hybridization intensity increased divided by the total number of base positions in the gene which are analyzed. The Dec Ratio column indicates the number of base positions where the hybridization intensity decreased divided by the total number of base positions in the gene which are analyzed. The Pos Change column indicates the difference in the number of positive scoring probe pairs in the experimental data versus the baseline data. The Neg Change column indicates the difference in the number of negative scoring probe pairs (perfect match and mismatch) in the experimental data versus the baseline data.

The Inc/Dec column indicates the number probe pairs which had an increase in hybridization intensity in the experimental data versus the number of probe pairs which had a decrease in hybridization intensity in the experimental data. The Avg Diff column indicates the average intensity difference in the experimental data.

The Diff Call column (not shown) indicates the change in expression level between the experiments for the gene. The column shows a "I" for increased gene expression, "MI" for marginal increased gene expression, "D" for decreased gene expression, "MD" for marginal decreased gene expression, "NC" for no change, and "?" for unknown. In a preferred embodiment, the change in expression level is calculated as described in reference to step 1326 of FIG. 26B.

In addition to calculating the change in gene expression, the user may also select graphs to analyze the data. Graphics display area 1402 shows three different graphs depicting the data from the baseline and experimental data.

Figure 28:
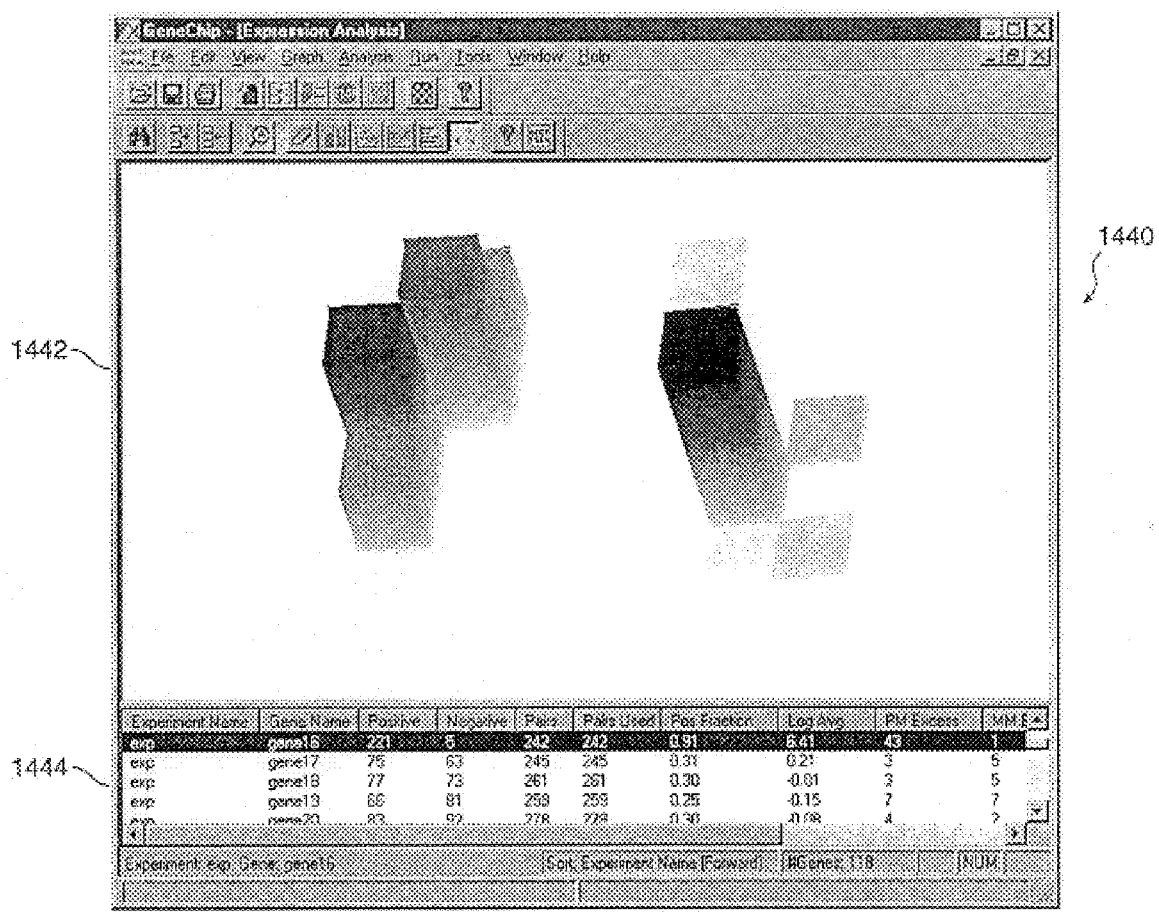
FIG. 28 shows a screen display illustrating a three-dimensional bar graph which illustrates the change of gene expression between experiments.

FIG. 28 shows a screen display illustrating a three-dimensional bar graph which illustrates the change of gene expression between experiments. A screen display 1440 displays a graphical display area 1442 including a three-dimensional bar graph of the expression level of selected genes in a data display area 1444. The user selects one or more genes in the data display area and then instructs the system to generate a three-dimensional bar graph of the expression level of these genes, where the expression level in a preferred embodiment is the average intensity difference (i.e., average(IDIF). The three-dimensional bar graph allows the user to easily view the expression level of multiple genes. Additionally, similar genes slected from multiple experiments may be shown simultaneously and rotated to display differences in experssion levels.

Conclusion

The above description is illustrative and not restrictive. Many variations of the invention will become apparent to those of skill in the art upon review of this disclosure. Merely by way of example, while the invention is illustrated with particular reference to the evaluation of DNA (natural or unnatural), the methods can be used in the analysis from chips with other materials synthesized thereon, such as RNA. The scope of the invention should, therefore, be determined not with reference to the above description, but instead should be determined with reference to the appended claims along with their full scope of equivalents.

What is claimed is:

1. A computer implemented method of generating a gene expression call of a gene of a sample nucleic acid sequence that is indicative of gene expression, the method comprising the steps of:

inputting a plurality of hybridization intensities of pairs of perfect match and mismatch probes, each pair of perfect match and mismatch probes corresponding to different portions of the gene, the perfect match probes being perfectly complementary to the gene and the mismatch probes having one base mismatch with the gene, and the hybridization intensities indicating hybridization affinity between the perfect match and mismatch probes and the sample nucleic acid sequence that is indicative of gene expression;

comparing the hybridization intensities of each pair of perfect match and mismatch probes; and generating a gene expression call of the sample nucleic acid sequence.

2. The computer implemented method of claim 1, further comprising the step of comparing a difference between hybridization intensities of perfect match and mismatch probes at a base position to a difference threshold.

3. The computer implemented method of claim 1, further comprising the step of comparing a quotient of hybridization intensities of perfect match and mismatch probes at a base position to a ratio threshold.

4. The computer implemented method of claim 1, further comprising the step of utilizing a decision matrix to determine the gene expression call.

5. The computer implemented method of claim 1, wherein the gene expression call is selected from the group consisting of expressed, marginal, and absent.

6. The computer implemented method of claim 1, further comprising displaying the gene expression call.

7. A computer implemented method of displaying a change in expression of a gene of a sample nucleic acid sequence that is indicative of gene expression, the method comprising the steps of:

inputting a plurality of hybridization intensities of pairs of perfect match and mismatch probes, each pair of perfect match and mismatch probes corresponding to different portions of the gene, the perfect match probes being perfectly complementary to the gene and the mismatch probes having one base mismatch with the gene, and the hybridization intensities indicating hybridization affinity between the perfect match and mismatch probes and the sample nucleic acid sequence that is indicative of gene expression;

comparing the hybridization intensities of each pair of perfect match and mismatch probes in order to generate a gene expression level of the sample nucleic acid sequence;

determining a change in expression by comparing the gene expression level to a baseline gene expression level; and displaying the change in expression of the gene in the sample nucleic acid.

8. The computer implemented method of claim 6, wherein the change in expression is displayed as a graph.

9. The computer implemented method of claim 6, further comprising the step of generating the baseline expression level according to the inputting and comparing steps of claim 7 for a different sample nucleic acid sequence.

10. The computer implemented method of claim 6, further comprising the step of comparing hybridization intensities of perfect match and mismatch probes hybridizing with the sample nucleic acid sequence and hybridization intensities of perfect match and mismatch probes hybridizing with a baseline sequence to a difference threshold.

11. The computer implemented method of claim 6, further comprising the step of comparing hybridization intensities of perfect match and mismatch probes hybridizing with the sample nucleic acid sequence and hybridization intensities of perfect match and mismatch probes hybridizing with a baseline sequence to a ratio threshold.

12. The computer implemented method of claim 6, further comprising the step of utilizing a decision matrix to determine the change in expression of the gene in the sample nucleic acid.

13. The computer implemented method of claim 6, wherein the change in expression of the gene in the sample nucleic acid is selected from the group consisting of increased, marginal increase, decreased, marginal decrease, and no change.

14. A computer implemented method of monitoring change in expression of a gene of a sample nucleic acid sequence that is indicative of gene expression, the method comprising the steps of:

inputting a plurality of hybridization intensities of pairs of perfect match and mismatch probes, each pair of perfect match and mismatch probes corresponding to different portions of the gene, the perfect match probes being perfectly complementary to the gene and the mismatch probes having at least one base mismatch with the gene, and the hybridization intensities indicating hybridization affinity between the perfect match and mismatch probes and the sample nucleic acid sequence that is indicative of gene expression;

comparing the hybridization intensities of each pair of perfect match and mismatch probes in order to generate a gene expression level of the sample nucleic acid sequence; and determining a change in expression by comparing the gene expression level to a baseline gene expression level.

15. The computer implemented method of claim 14, further comprising the step of generating the baseline expression level according to the inputting and comparing steps of claim 14 for a different sample nucleic acid sequence.

16. The computer implemented method of claim 14, further comprising the step of comparing hybridization intensities of perfect match and mismatch probes hybridizing with the sample nucleic acid sequence and hybridization intensities of perfect match and mismatch probes hybridizing with a baseline sequence to a difference threshold.

17. The computer implemented method of claim 14, further comprising the step of comparing hybridization intensities of perfect match and mismatch probes hybridizing with the sample nucleic acid sequence and hybridization intensities of perfect match and mismatch probes hybridizing with a baseline sequence to a ratio threshold.

18. The computer implemented method of claim 14, further comprising the step of utilizing a decision matrix to determine the change in expression of the gene in the sample nucleic acid.

19. The computer implemented method of claim 14, wherein the change in expression of the gene in the sample nucleic acid is selected from the group consisting of increased, marginal increase, decreased, marginal decrease, and no change.

* * * * *